(12) United States Patent
Mechoulam et al.

(10) Patent No.: US 8,497,299 B2
(45) Date of Patent: Jul. 30, 2013

(54) COMPOSITIONS INCLUDING QUINONOID DERIVATIVES OF CANNABINOIDS FOR THERAPEUTIC USE

(75) Inventors: Raphael Mechoulam, Jerusalem (IL); Natalya M. Kogan, Jerusalem (IL); Ruth Rabinowitz, Jerusalem (IL); Michael Schlesinger, Jerusalem (IL)

(73) Assignee: Yissum Research Development Company of The Hebrew University of Jerusalem, Jerusalem (IL)

( * ) Notice: Subject to any disclaimer, the term of this patent is extended or adjusted under 35 U.S.C. 154(b) by 1442 days.

(21) Appl. No.: 10/597,166

(22) PCT Filed: Jan. 14, 2005

(86) PCT No.: PCT/IL2005/000053
§ 371 (c)(1),
(2), (4) Date: Nov. 16, 2009

(87) PCT Pub. No.: WO2005/067917
PCT Pub. Date: Jul. 28, 2005

(65) Prior Publication Data
US 2011/0092584 A1     Apr. 21, 2011

(30) Foreign Application Priority Data

Jan. 15, 2004  (IL) ........................................ 159892

(51) Int. Cl.
*A61K 31/35* (2006.01)
*C07D 311/80* (2006.01)
(52) U.S. Cl.
USPC ........................................ 514/454; 549/391
(58) Field of Classification Search
USPC ...... 514/298, 437, 454; 549/26, 391; 546/108
See application file for complete search history.

(56) References Cited

FOREIGN PATENT DOCUMENTS
WO           01/95899 A2      12/2001

OTHER PUBLICATIONS

Barth, F. and Rinaldi-Carmona, M., Curr. Med. Chem., 1999, pp. 745-755, vol. 6.
Mechoulam, R. et al., Tetrahedron, 1968, pp. 5615-5624, vol. 24.
Zajicek, J., Lancet Neural., 2002, p. 147, vol. 1.
Di Carlo, G. and Izzo, A.A., Expert Opin. Investig. Drugs, 2003, pp. 39-49, vol. 12.
Croxford, J.L., CNS Drugs, 2003, pp. 179-202, vol. 17.
Ollinger, K. and Kagedal, K., Subcell. Biochem., 2002, pp. 151-170, vol. 36.
Gerwitz, D.A., Biochem. Pharmacol., 1999, pp. 727-741, vol. 57.
Carmichael, J. et al., Cancer Res., 1987, pp. 936-942, vol. 47.
Rubinstein, L.V. et al., J. Natl. Cancer Inst., 1990, pp. 1113-1118, vol. 82.
Rubnov, S. et al., J. Nat. Prod., 2001, pp. 993-996, vol. 64.
Kazuhito Watanabe et al, 1991, vol. 14, pp. 421-427, Inhibitory Effect of Cannabidiol Hydroxy-quinone, an Oxidative Product of Canabidiol, on the Hepatic Microsomal Drug-Metabolizing Enzymes of Mice, J. Pharmacobio-Dyn.
Lee. K.H., Medicinal Research Reviews, 1999, pp. 569-596, vol. 19.
Naturally Occuring Quinones, Routledge, Chapman & Hall, Incorporated, 1987, Ed. R.H. Thomson.
Bolton et al., Chemical Resarch in Toxicology, 2000, pp. 135-160, vol. 13.
Begleiter, A., Frontiers in Bioscience, 2000, pp. E153-E171, vol. 5.
Aubel-Sadron, G. and Landos-Gagliardi, D., Biochimie, 1984, pp. 333-352, vol. 66.
Di Marco et al., Cancer Treat. Rep., 1981, pp. 3-8, vol. 65.
Zucchi, R. and Danesi, R., Curr. Med. Chem. Anti-Canc. Agents, 2003, pp. 151-171, vol. 3.
Thomas, X. et al., Ann. Hemathol., 2002, pp. 504-507, vol. 81.
Razdan, R.K., Pharmacol, Rev., 1986, pp. 75-149, vol. 38.
Mechoulam et al., Progress in Med. Chem., 1998, pp. 199-243, vol. 35.
Hadjat-Kashani et al., Heterocycles, 1986, pp. 1973-1976, vol. 24.
Tamura, Y. et al., Synthesis, 1989, pp. 126-127.
Akai, S. and Kita, Y., Org. Prep. Procedures Inl., 1998, pp. 603-629, vol. 30.
Barret, R. and Daudon, M., Tetrahedron Letters, 1990, pp. 4871-4872, vol. 31.
Kato, N. et al., Synthesis, 1997, pp. 625-627.
Barret, R. and Daudon, M., Synth. commun., 1990, pp. 2907-2912, vol. 20.
Capdevielle, P. and Maumy, M., Tetrahedron Letters, 1982, pp. 1577-1580, vo.23.
Reynolds, W.F. and Enriquez, R.G., J. Nat. Prod., 2002, pp. 221-244, vol. 65.
Kock, M. et al., Tetrahedron Letters, 1996, pp. 363-366, vol. 37.
Reif, B. et al., JMRA, 1996, pp. 282-285, vol. 118.
Usami, N. et al., Research Communication in Alcohol and Substance of Abuse, 1997, pp. 125-139, vol. 18(3&4).
Usami, N. et al., Research Communication in Alcohol and Substance of Abuse, 1999, pp. 53-68, vol. 20(1&2).
Edery, H. et al., Ann. NY Acad. Sci., 1971, pp. 40-53, vol. 191.
Edery, H. et al., Arzneimittel-Forschung, 1972, pp. 1995-2003, vol. 22(11).
Watanabe, K. et al., J. Pharm. Dyn., 1991, pp. 421-427, vol. 14(7).
Honorio K.M. et al., Theochem., 2001, pp. 99-106, vol. 538.
Bornheim, L. et al., Chem. Res. Toxicol., 1998, pp. 1209-1216, vol. 11(10).
Kogan, N. et al., J. Med. Chem., 2004, pp. 3800-3808, vol. 47(15).
Naturally Occuring Quinones, Kluwer Academic Publishers, 1986, Ed. R.H. Thomson.
Stites et al., Journal of Nutrition, 2002, pp. 719-727, vol. 132.
Natalya M. Kogan et al, "Synthesis and Antitumor Activity of Quinonoid Derivatives of Cannabinoids", 2004, vol. 17, pp. 3800-3806, J.Med. Chem.

*Primary Examiner* — Sreeni Padmanabhan
*Assistant Examiner* — Jody Karol
(74) *Attorney, Agent, or Firm* — Martin Fleit; Paul D. Bianco; Fleit Gibbons Gutman Bongini & Bianco PL

(57) ABSTRACT

The present invention relates to cannabinoic quinone compounds, and especially to their medical use. In particular five cannabinoic quinones, designated HU-331, HU-336, HU-345, HU-395 and HU-396, are described as active agents in pharmaceutical compositions. These compounds and compositions thereof are intended for the treatment of inflammatory, infectious, auto-immune and particularly hyperproliferative disorders. Thus, the compounds of the invention may be used as anti-tumor agents, or for the treatment of cancer. Furthermore, three of these compounds, HU-345, HU-395 and HU-396, are novel cannabinoic quinones.

17 Claims, 13 Drawing Sheets

COMPOSITIONS INCLUDING QUINONOID DERIVATIVES OF CANNABINOIDS FOR THERAPEUTIC USE

FIELD OF THE INVENTION

The present invention relates to the field of cannabinoids. More specifically, the present invention describes the medical use of some quinonoid derivatives of cannabinoids, as well as some such novel compounds.

BACKGROUND OF THE INVENTION

All publications mentioned throughout this application are fully incorporated herein by reference, including all references cited therein.

Quinones of various chemical families, present in plants and animals, serve as biological modulators [Routledge et al. (1996) *Naturally Occurring Quinones*, Kluwer Academic Publishers; Stites et al. (2002) *Journal of Nutrition* 132, 719-727; Lee, K. H. (1999) *Medicinal Research Reviews* 19, 569-596; Thomson, R. H. (1987) *Naturally Occurring Quinones*, Routledge, Chapman & Hall, Incorporated; Bolton et al. (2000) *Chemical Research in Toxicology* 13, 135-160] and both natural and synthetic quinones are widely used as drugs. Anthracyclines, a large group of quinonoid compounds produced by different strains of *Streptomyces*, exert antibiotic and antineoplasic effects and are used to treat some forms of cancer [Begleiter, A. (2000) *Frontiers in Bioscience* 5, E153-E171; Aubel-Sadron, G. and Landos-Gagliardi, D. (1984) *Biochimie* 66, 333-352]. The best known members of this family are daunorubicin and doxorubicin, the first identified anthracyclins [Di Marco et al. (1981) *Cancer Treat Rep* 65, 3-8]. Other quinones are also used as anticancer drugs. Mitomycin C and streptonigrin produced by *Streptomyces* and the synthetic epirubicin and mitoxantron are well known examples. Although these and other quinonoid compounds are effective in the treatment of many different forms of cancer, their side effects—the most severe of them being cumulative heart toxicity—limit their use. Thus, development of quinonoid compounds that display antineoplastic activity, but are less toxic, is a major therapeutic goal [Zucchi, R., Danesi, R. (2003) *Curr Med Chem Anti-Canc Agents* 3, 151-171; Thomas, X. et al. (2002) *Ann Hemathol* 81, 504-507].

A large number of cannabinoids have been synthesized and tested in the in vitro and in vivo models of various diseases [Razdan, R. K. (1986) *Pharmacol Rev.* 38, 75-149; Mechoulam, et al. (1998) *Progress in Med Chem* 35, 199-243; Barth, F., Rinaldi-Carmona, M. (1999) *Curr Med Chem.* 6, 745-55]. In the present study, five cannabinoic quinones, two of which were originally prepared by the inventors to investigate the chemical basis of the Beam test (a color test for cannabinoids) [Mechoulam, R. et al. (1968) *Tetrahedron* 24, 5615-5624], and three novel cannabinoic quinones which are disclosed herein, were evaluated as medicinal agents. In particular, the present inventors wished to find cannabinoic quinones which would present biological and therapeutic activity, with minimized side effects, a major problem usually found in these compounds.

The present report encompasses the medicinal properties of these quinone cannabinoid derivatives, especially with regards to their potent antineoplastic activity both in vitro and in vivo, with no measurable side-effects.

Thus, it is an object of the present invention to provide pharmaceutical compositions comprising cannabinoic quinones as the active agent. It is a further object to provide said compounds as anti-neoplastic or anti-cancer drugs. Other uses and objects of the invention will become clear as the description proceeds.

SUMMARY OF THE INVENTION

In a first aspect, the present invention relates to a pharmaceutical composition comprising as active agent a cannabinoic quinone, wherein said cannabinoic quinone is defined by general formula (I):

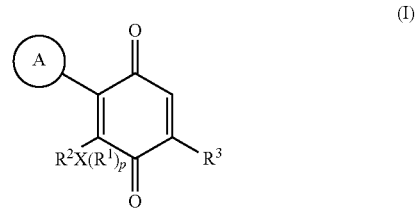

(I)

wherein, ring A is 5-, 6-, or 7-membered alicyclic or aromatic ring optionally substituted with from 1 to 3 substituents independently selected from optionally branched $C_1$-$C_5$ alkyl, optionally branched $C_1$-$C_5$ alkenyl, hydroxy, alkoxy, halo (fluoro, chloro, bromo, iodo), thio, amino and cyano;

X is an oxygen, nitrogen or sulfur atom;

p is zero when X is oxygen or sulfur, or p is 1 when X is nitrogen;

$R^1$ is H or $C_1$-$C_5$ alkyl;

$R^2$ designates a substituent selected from H and $C_1$-$C_5$ alkyl, or $R^2$ designates an optionally branched $C_1$-$C_5$ alkylene connected to ring A forming a 6-membered heterocyclic ring comprising atom X, two carbon atoms of the quinone ring to which X is attached and carbon atoms 3 and 4 of ring A; and $R^3$ is optionally branched $C_1$-$C_{10}$ alkyl or optionally branched $C_1$-$C_{10}$ alkenyl, wherein said alkyl or alkenyl are optionally substituted with hydroxyl, alkoxy, halo (fluoro, chloro, bromo, iodo), thio, amino or cyano;

and optionally further comprising at least one pharmaceutically acceptable additive, diluent and/or carrier.

In one preferred embodiment, said cannabinoic quinone is the compound of formula II:

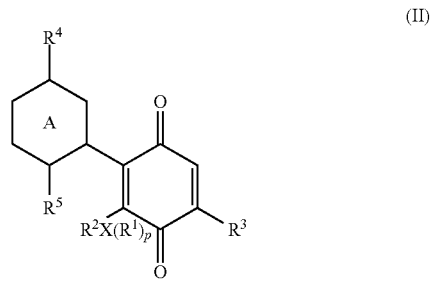

(II)

wherein ring A is a cyclohexane, cyclohexene or benzene ring;

X is an oxygen, nitrogen or sulfur atom;

p is zero when X is oxygen or sulfur, or p is 1 when X is nitrogen;

$R^1$ is H or $C_1$-$C_5$ alkyl;

$R^2$ designates a substituent selected from H and $C_1$-$C_5$ alkyl, or $R^2$ designates an optionally branched $C_1$-$C_5$ alkylene connected to ring A forming a 6-membered heterocyclic ring comprising atom X, two carbon atoms of the quinone ring to which X is attached and carbon atoms 3 and 4 of ring A;

$R^3$ is optionally branched $C_3$-$C_9$ alkyl or optionally branched $C_3$-$C_9$ alkenyl, wherein said alkyl or alkenyl are optionally substituted with hydroxyl, alkoxy, halo (fluoro, chloro, bromo, iodo), thio, amino or cyano;

$R^4$ is optionally branched $C_1$-$C_5$ alkyl or optionally branched $C_1$-$C_5$ alkenyl, optionally substituted with hydroxyl, halo (fluoro, chloro, bromo, iodo) thio, amino and cyano; and $R^5$ is optionally branched $C_1$-$C_5$ alkyl or optionally branched $C_1$-$C_5$ alkenyl, or $R^5$ is hydrogen when $R^2$ is alkylene.

In one specific embodiment, the cannabinoic quinone is a compound of one of formulae (III), (IV) or (V), wherein compounds of formulae (III) and (IV) have the structure:

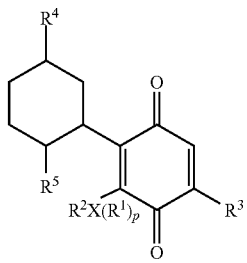

(III)

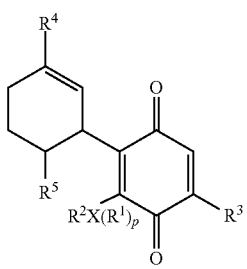

(IV)

wherein,

X is an oxygen, nitrogen or sulfur atom;

p is zero when X is oxygen or sulfur, or p is 1 when X is nitrogen;

$R^1$ is H or $C_1$-$C_5$ alkyl;

$R^2$ designates a substituent selected from H and $C_1$-$C_5$ alkyl;

$R^3$ is optionally branched $C_1$-$C_{10}$ alkyl or optionally branched $C_1$-$C_{10}$ alkenyl, wherein said alkyl or alkenyl are optionally substituted with hydroxyl, alkoxy, halo (fluoro, chloro, bromo, iodo), thio, amino or cyano; and $R^4$ is optionally branched $C_1$-$C_5$ alkyl or optionally branched $C_1$-$C_5$ alkenyl, optionally substituted with hydroxyl, halo (fluoro, chloro, bromo, iodo) thio, amino and cyano; and $R^5$ is optionally branched $C_1$-$C_5$ alkyl, optionally branched $C_1$-$C_5$ alkenyl; and compound of formula (V) has the following structure:

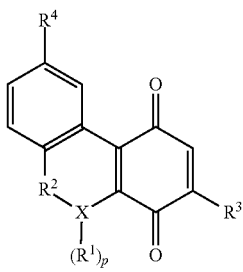

(V)

wherein

X is an oxygen, nitrogen or sulfur atom;

p is zero when X is oxygen or sulfur, or p is 1 when X is nitrogen;

$R^1$ is H or $C_1$-$C_5$ alkyl;

$R^2$ designates a methylene group optionally substituted with up to two alkyl groups, wherein $R^2$ with the substituents comprises up to 5 carbon atoms;

$R^3$ is optionally branched $C_1$-$C_{10}$ alkyl or optionally branched $C_1$-$C_{10}$ alkenyl, wherein said alkyl or alkenyl are optionally substituted with hydroxyl, alkoxy, halo (fluoro, chloro, bromo, iodo), thio, amino or cyano; and $R^4$ is optionally branched $C_1$-$C_5$ alkyl or optionally branched $C_1$-$C_5$ alkenyl, optionally substituted with hydroxyl, halo (fluoro, chloro, bromo, iodo) thio, amino and cyano.

In most preferred embodiments of the cannabinoic quinones of the invention, X is oxygen, $R^2$ is hydrogen, and $R^5$ is 2-propyl or 2-propenyl. Alternatively, X is an oxygen atom forming a pyrane ring comprising two carbon atoms of the quinone ring to which said oxygen is attached and carbon atoms 3 and 4 of ring A, which pyrane ring is preferably 2,2-dimethyl substituted. Yet in a further most preferred embodiment, $R^4$ is methyl. Cannabinoic quinones of the invention include optically active isomers, and racemic mixtures, of each of the compounds of formulae I, II, III, IV, and V.

The present invention describes five cannabinoid-derived quinones in particular, which were synthesized by the inventors and are referred to herein as 3S,4R-p-benzoquinone-3-hydroxy-2-p-mentha-(1,8)-dien-3-yl-5-pentyl (also designated HU-331), 6aR,10aR-1-H-dibenzo[b,d]pyran-1,4-(6H)-dione-6aβ,7,10,10aα-tetrahydro-6,6,9-trimethyl-3-pentyl (also designated HU-336), 1-H-dibenzo[b,d]pyran-1,4(6H)-dione-6,6,9-trimethyl-3-pentyl (also designated HU-345), 3S,4R-p-benzoquinone-3-hydroxy-2-[p-mentha-1-en-3-yl]-5-pentyl (also designated HU-395), and 3S,4R-p-benzoquinone-3-hydroxy-2-[p-menthan-3-yl]-5-pentyl (also designated HU-396).

The present invention refers to the use of compounds of formulae (I), (II), (III), (IV) and (V) above, and specifically compounds HU-331, HU-336, HU-345, HU-395 and HU-396, in the preparation of a medicament.

Thus, the pharmaceutical composition of the invention, or said medicament, may be for the treatment of hyperproliferative disorders such as carcinomas, lymphomas, melanomas, glioblastomas and sarcomas. Alternatively, the pharmaceutical composition of the invention may be for the treatment of a non-malignant hyperproliferative disorder, for example psoriasis.

The pharmaceutical composition of the invention may optionally further comprise carriers, additives and diluents. In preferred embodiments, the pharmaceutical compositions of the invention comprise a pharmaceutically acceptable vehicle or carrier, particularly a mixture of ethanol:Emulphor®: phosphate buffered saline (PBS), at 1:1:18 v/v ratio.

The pharmaceutical compositions of the invention, comprising as active agent cannabinoid quinones, may also be used in the treatment of conditions such as inflammations, autoimmune diseases (for example multiple sclerosis) and infections, particularly infections caused by infectious agents like bacteria (Gram positive and Gram negative, mycobacteria, etc.), protozoa and fungus In another aspect, the present invention relates to a method for the treatment of a hyperproliferative disorder, malignant or non-malignant, comprising administering an therapeutic effective amount of a cannabinoic quinone or of a pharmaceutical composition thereof to a subject in need.

Thus, the present invention provides a cannabinoic quinone, preferably HU-331, or compositions comprising the same, to be used in the treatment of hyperproliferative disorders, particularly colon cancer, lymphoma and breast cancer.

In a further aspect, the present invention provides a method for the treatment of conditions selected from the group consisting of inflammations, autoimmune diseases (in particular multiple sclerosis), and infections, particularly infections caused by infectious agents such as bacteria (including gram positive and gram negative bacteria, mycobacteria, etc.), protozoa and fungus, wherein said method comprises administering a therapeutic effective amount of a cannabinoic quinone or of a pharmaceutical composition thereof to a subject in need.

In a later aspect, the present invention also presents the use of a cannabinoic quinone for the preparation of a pharmaceutical composition, wherein said cannabinoic quinone is any one of HU-331, HU-336, HU-345, HU-395 and HU-396. Preferably, said cannabinoic quinone is HU-331.

Lastly, the present invention provides compounds of formulae (III), (IV) and (V). Compounds of formulae (III) and (IV) are:

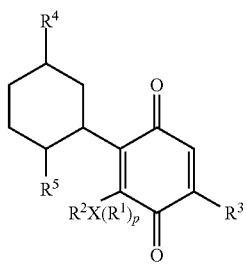

(III)

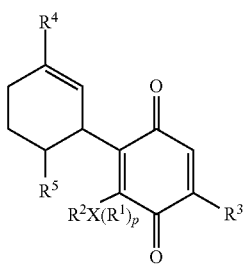

(IV)

wherein
X is an oxygen, nitrogen or sulfur atom;
p is zero when X is oxygen or sulfur, or p is 1 when X is nitrogen;
$R^1$ is H or $C_1$-$C_5$ alkyl;

$R^2$ designates a substituent selected from H and $C_1$-$C_5$ alkyl;

$R^3$ is optionally branched $C_1$-$C_{10}$ alkyl or optionally branched $C_1$-$C_{10}$ alkenyl, wherein said alkyl or alkenyl are optionally substituted with hydroxyl, alkoxy, halo (fluoro, chloro, bromo, iodo), thio, amino or cyano; and $R^4$ is optionally branched $C_1$-$C_5$ alkyl or optionally branched $C_1$-$C_5$ alkenyl, optionally substituted with hydroxyl, halo (fluoro, chloro, bromo, iodo) thio, amino and cyano; and $R^5$ is optionally branched $C_1$-$C_5$ alkyl or optionally branched $C_1$-$C_5$ alkenyl.

Compound of formula (V) is:

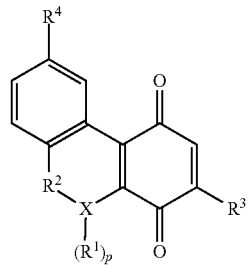

(V)

wherein,
X is an oxygen, nitrogen or sulfur atom;
p is zero when X is oxygen or sulfur, or p is 1 when X is nitrogen;
$R^1$ is H or $C_1$-$C_5$ alkyl;
$R^2$ designates a methylene group optionally substituted with up to two alkyl groups, wherein $R^2$ with the substituents comprises up to 5 carbon atoms;
$R^3$ is optionally branched $C_1$-$C_{10}$ alkyl or optionally branched $C_1$-$C_{10}$ alkenyl, wherein said alkyl or alkenyl are optionally substituted with hydroxyl, alkoxy, halo (fluoro, chloro, bromo, iodo), thio, amino or cyano; and $R^4$ is optionally branched $C_1$-$C_5$ alkyl or optionally branched $C_1$-$C_5$ alkenyl, optionally substituted with hydroxyl, halo (fluoro, chloro, bromo, iodo) thio, amino and cyano.

Preferred compounds of formulae (IV) and (III) are 3S,4R-p-benzoquinone-3-hydroxy-2-[p-mentha-1-en-3-yl]-5-pentyl and 3S,4R-p-benzoquinone-3-hydroxy-2-[p-menthan-3-yl]-5-pentyl, of formulae:

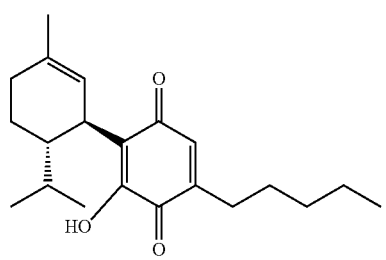 [SMILES: CCCCCC1=CC(=O)C([C@@H]2C=C(C)CC[C@H]2C(C)C)=C(O)C1=O]

also designated HU-395; and

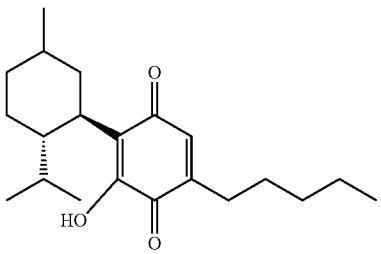 [SMILES: CCCCCC1=CC(=O)C([C@@H]2CC(C)CC[C@H]2C(C)C)=C(O)C1=O]

also designated HU-396, respectively.

The preferred compound of formula (V) is 1-H-dibenzo[b,d]pyran-1,4(6H)-dione-6,6,9-trimethyl-3-pentyl, of formula:

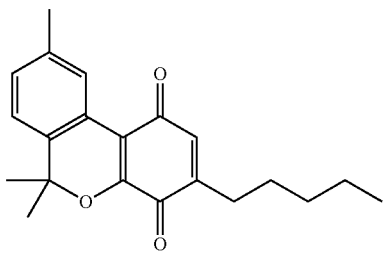 [SMILES: CCCCCC1=CC(=O)C2=C(OC(C)(C)c3ccc(C)cc32)C1=O]

also designated HU-345.

BRIEF DESCRIPTION OF THE FIGURES

FIG. 1A: Synthesis of HU-331.
FIG. 1B: Synthesis of HU-336.
FIG. 1C: Synthesis of HU-345.
FIG. 1D: Synthesis of HU-395.
FIG. 1E: Synthesis of HU-396.
FIG. 2A: $^1$H NMR of HU-336.
FIG. 2B: HU-336.
FIG. 5A: HU-336 inhibition of human cancer cell lines in vitro.
FIG. 5B: HU-331 inhibition of human cancer cell lines in vitro.
FIG. 5C: HU-345 inhibition of human cancer cell lines in vitro.
FIG. 5D: HU-395 inhibition of Jurkat cell growth in vitro.
FIG. 5E: HU-396 inhibition of Jurkat cell growth in vitro.
Abbreviations: Inhib., inhibition; conc., concentration.
FIG. 6A: Effect of HU-331 via intraperitoneal (i.p.) on the growth of HT-29 colon cancer in nude mice.
FIG. 6B: Effect of HU-331 on the growth of HT-29 colon cancer in nude mice, upon subcutaneous (s.c.) or intra-tumor administration.
Abbreviations: Tu. Si., tumor size; D., days; cont., control.
FIG. 7A: Photograph of the tumor in situ.
FIG. 7B: Photograph of the tumor in higher magnification.
Abbreviations: cont., control.

DETAILED DESCRIPTION OF THE INVENTION

Figure 1A:
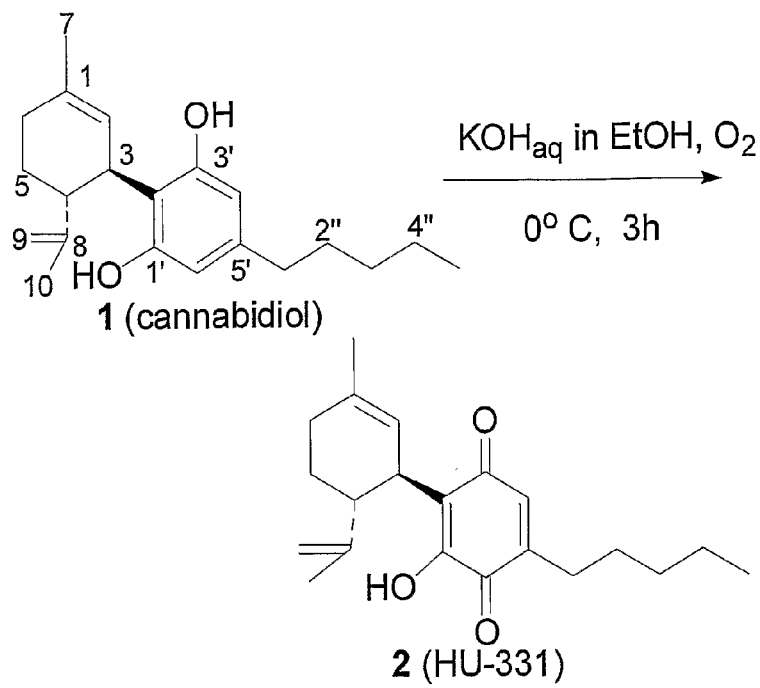
FIG. 1A-1E: Synthesis of the cannabinoic quinones.
Figure 1B:
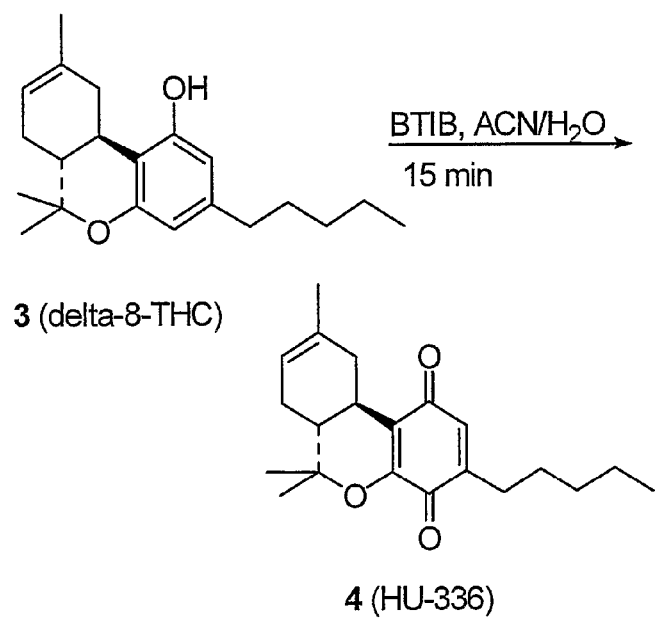
Figure 1C:
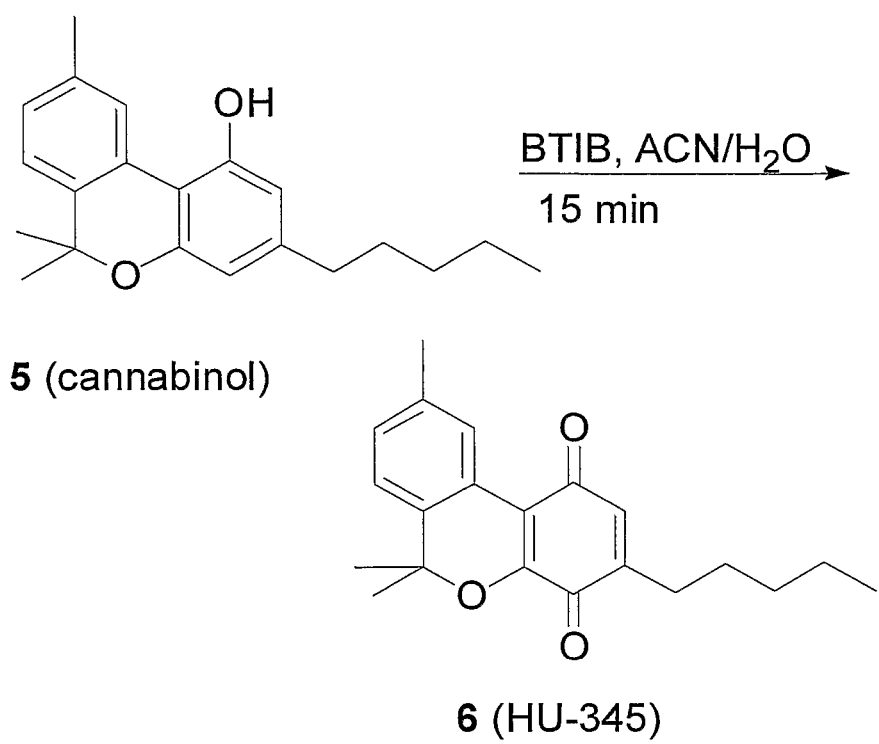
Figure 1D:
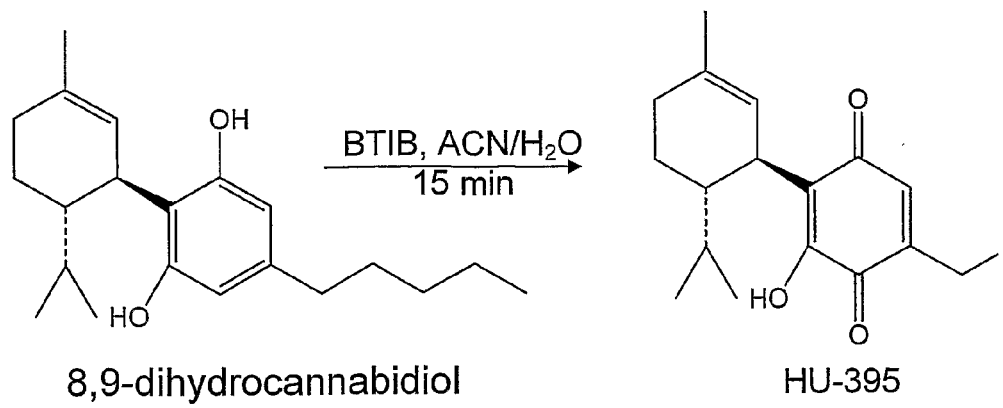
Figure 1E:
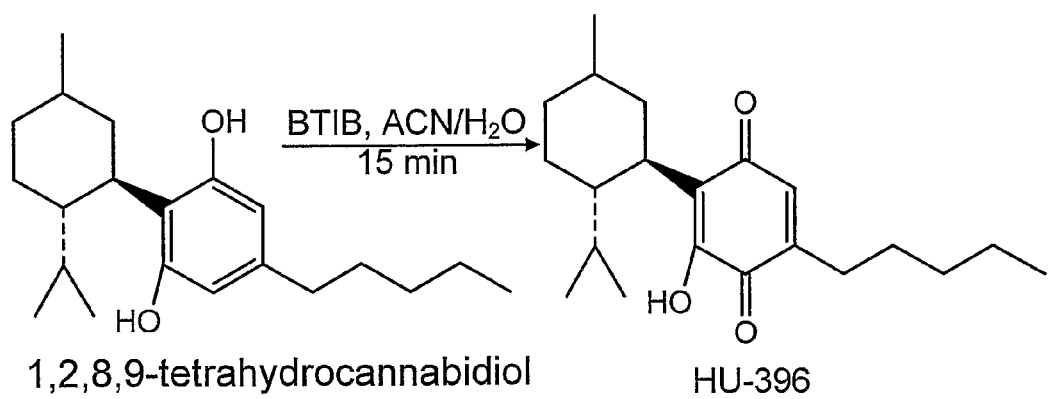

Quinones of various chemical families, present in plants and animals, serve as biological modulators.

Although a large number of cannabinoids have been synthesized and tested in the in vitro and in vivo models of diseases [for recent examples see Zajicek, J. (2002) *Lancet Neurol* 1, 147; Di Carlo, G. and Izzo, A. A. (2003) *Expert Opin Investig Drugs*. 12, 39-49; Croxford, J. L. (2003) *CNS Drugs*. 17, 179-202], and both natural and synthetic quinones are widely used as drugs, the pharmacological potential of cannabinoid-derived quinones has not yet been investigated. In this light, the present inventors set forth to examine the pharmacological activity of cannabinoid-derived quinones.

Thus, the present invention provides cannabinoic quinones of the general formula:

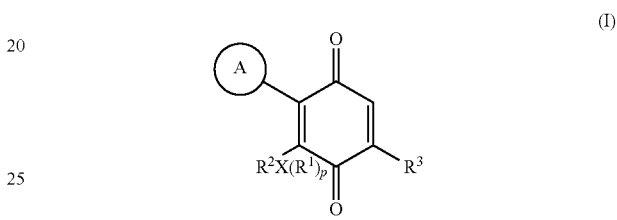

(I)

wherein, ring A is 5-, 6-, or 7-membered alicyclic or aromatic ring optionally substituted with from 1 to 3 substituents independently selected from optionally branched $C_1$-$C_5$ alkyl, optionally branched $C_1$-$C_5$ alkenyl, hydroxy, alkoxy, halo (fluoro, chloro, bromo, iodo), thio, amino and cyano;

X is an oxygen, nitrogen or sulfur atom;

p is zero when X is oxygen or sulfur, or p is 1 when X is nitrogen;

$R^1$ is H or $C_1$-$C_5$ alkyl;

$R^2$ designates a substituent selected from H and $C_1$-$C_5$ alkyl, or $R^2$ designates an optionally branched $C_1$-$C_5$ alkylene connected to ring A forming a 6-membered heterocyclic ring comprising atom X, two carbon atoms of the quinone ring to which X is attached and carbon atoms 3 and 4 of ring A; and $R^3$ is optionally branched $C_1$-$C_{10}$ alkyl or optionally branched $C_1$-$C_{10}$ alkenyl, wherein said alkyl or alkenyl are optionally substituted with hydroxyl, alkoxy, halo (fluoro, chloro, bromo, iodo), thio, amino or cyano;

and optionally further comprising at least one pharmaceutically acceptable additive, diluent and/or carrier.

Thus, in a first aspect, the present invention relates to a pharmaceutical composition comprising as active agent a cannabinoic quinone, wherein said cannabinoic quinone is defined by general formula (I):

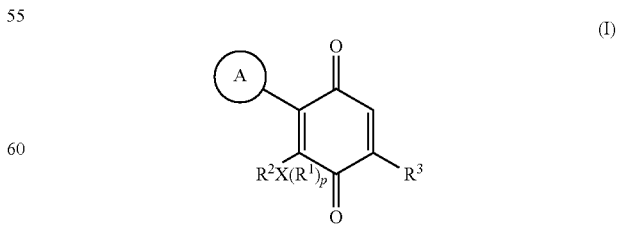

(I)

wherein, ring A is 5-, 6-, or 7-membered alicyclic or aromatic ring optionally substituted with from 1 to 3 substituents independently selected from optionally branched $C_1$-$C_5$ alkyl, optionally branched $C_1$-$C_5$ alkenyl, hydroxy, alkoxy, halo (fluoro, chloro, bromo, iodo), thio, amino and cyano;

X is an oxygen, nitrogen or sulfur atom;

p is zero when X is oxygen or sulfur, or p is 1 when X is nitrogen;

$R^1$ is H or $C_1$-$C_5$ alkyl;

$R^2$ designates a substituent selected from H and $C_1$-$C_5$ alkyl, or $R^2$ designates an optionally branched $C_1$-$C_5$ alkylene connected to ring A forming a 6-membered heterocyclic ring comprising atom X, two carbon atoms of the quinone ring to which X is attached and carbon atoms 3 and 4 of ring A; and $R^3$ is optionally branched $C_1$-$C_{10}$ alkyl or optionally branched $C_1$-$C_{10}$ alkenyl, wherein said alkyl or alkenyl are optionally substituted with hydroxyl, alkoxy, halo (fluoro, chloro, bromo, iodo), thio, amino or cyano;

and optionally further comprising at least one pharmaceutically acceptable additive, diluent and/or carrier.

By quinones of the above formula it is meant also the racemate, optically pure enantiomers, and non-racemic mixtures of the enantiomers.

As referred to herein, the term "alkyl" refers to a cyclic, branched or straight chain alkyl group containing only carbon and hydrogen, and unless otherwise mentioned contains one to twelve carbon atoms. Examples of alkyl groups are methyl, ethyl, n-propyl, isobutyl, t-butyl, pentyl, pivalyl, heptyl, adamantyl and cyclopentyl. Alkyl groups may either be unsubstituted or substituted with one or more substituents, eg. hydroxyl, alkoxy, halo, (fluoro, chloro, bromo, iodo), thio, amino and cyano.

As referred to herein, the term "lower alkyl" refers to a cyclic, branched or straight chain monovalent alkyl radical of one to five carbon atoms.

In one preferred embodiment, said cannabinoic quinone is the compound of formula II:

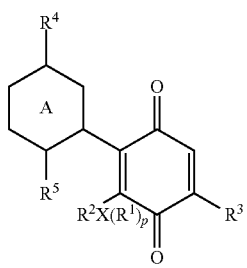

(II)

wherein ring A is a cyclohexane, cyclohexene or benzene ring;

X is an oxygen, nitrogen or sulfur atom;

p is zero when X is oxygen or sulfur, or p is 1 when X is nitrogen;

$R^1$ is H or $C_1$-$C_5$ alkyl;

$R^2$ designates a substituent selected from H and $C_1$-$C_5$ alkyl, or $R^2$ designates an optionally branched $C_1$-$C_5$ alkylene connected to ring A forming a 6-membered heterocyclic ring comprising atom X, two carbon atoms of the quinone ring to which X is attached and carbon atoms 3 and 4 of ring A;

$R^3$ is optionally branched $C_3$-$C_9$ alkyl or optionally branched $C_3$-$C_9$ alkenyl, wherein said alkyl or alkenyl are optionally substituted with hydroxyl, alkoxy, halo (fluoro, chloro, bromo, iodo), thio, amino or cyano;

$R^4$ is optionally branched $C_1$-$C_5$ alkyl or optionally branched $C_1$-$C_5$ alkenyl, optionally substituted with hydroxyl, halo (fluoro, chloro, bromo, iodo) thio, amino and cyano; and $R^5$ is optionally branched $C_1$-$C_5$ alkyl or optionally branched $C_1$-$C_5$ alkenyl, or $R^5$ is hydrogen when $R^2$ is alkylene.

It will be appreciated by those skilled in the art that the quinones of the present invention may contain at least one chiral center. Accordingly, the quinones used in the pharmaceutical compositions and methods of the present invention may exist, be isolated and/or synthesized in optically-active or racemic forms. Some quinones may also exhibit polymorphism. It is to be understood that the present invention encompasses any racemic, optically-active, polymorphic, or stereoisomeric form, or mixtures thereof, which form possesses medicinal properties, as defined herein.

Thus, in one embodiment, the quinones of the present invention are the pure (R)-isomers. In another embodiment, the quinones of the present invention are the pure (S)-isomers. In yet another embodiment, the quinones of the present invention are a mixture of the (R) and the (S) isomers. Alternatively, the quinones of the present invention are a racemic mixture comprising an equal amount of the (R) and the (S) isomers. It is well known in the art how to prepare optically-active forms (for example, by resolution of the racemic form by recrystallization techniques, by synthesis from optically-active starting materials, by chiral synthesis, or by chromatographic separation using a chiral stationary phase).

In one specific embodiment, the cannabinoic quinone is a compound of one of formulae (III), (IV) or (V), wherein compounds of formulae (III) and (IV) have the structure:

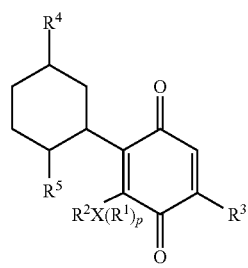

(III)

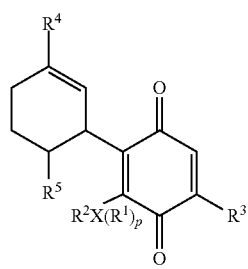

(IV)

wherein,

X is an oxygen, nitrogen or sulfur atom;

p is zero when X is oxygen or sulfur, or p is 1 when X is nitrogen;

$R^1$ is H or $C_1$-$C_5$ alkyl;

$R^2$ designates a substituent selected from H and $C_1$-$C_5$ alkyl;

$R^3$ is optionally branched $C_1$-$C_{10}$ alkyl or optionally branched $C_1$-$C_{10}$ alkenyl, wherein said alkyl or alkenyl are optionally substituted with hydroxyl, alkoxy, halo (fluoro, chloro, bromo, iodo), thio, amino or cyano; and $R^4$ is optionally branched $C_1$-$C_5$ alkyl or optionally branched $C_1$-$C_5$ alkenyl, optionally substituted with hydroxyl, halo (fluoro, chloro, bromo, iodo) thio, amino and cyano; and $R^5$ is optionally branched $C_1$-$C_5$ alkyl or optionally branched $C_1$-$C_5$ alkenyl;

and compound of formula (V) has the following structure:

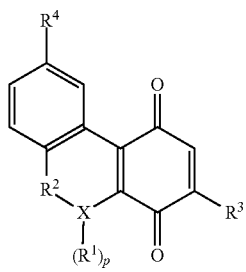

(V)

wherein

X is an oxygen, nitrogen or sulfur atom;

p is zero when X is oxygen or sulfur, or p is 1 when X is nitrogen;

$R^1$ is H or $C_1$-$C_5$ alkyl;

$R^2$ designates a methylene group optionally substituted with up to two alkyl groups, wherein $R^2$ with the substituents comprises up to 5 carbon atoms;

$R^3$ is optionally branched $C_1$-$C_{10}$ alkyl or optionally branched $C_1$-$C_{10}$ alkenyl, wherein said alkyl or alkenyl are optionally substituted with hydroxyl, alkoxy, halo (fluoro, chloro, bromo, iodo), thio, amino or cyano; and $R^4$ is optionally branched $C_1$-$C_5$ alkyl or optionally branched $C_1$-$C_5$ alkenyl, optionally substituted with hydroxyl, halo (fluoro, chloro, bromo, iodo) thio, amino and cyano.

In most preferred embodiments of the cannabinoic quinones of the invention, X is oxygen, $R^2$ is hydrogen, and $R^5$ is 2-propyl or 2-propenyl.

Alternatively, X is an oxygen atom forming a pyrane ring comprising two carbon atoms of the quinone ring to which said oxygen is attached and carbon atoms 3 and 4 of ring A, which pyrane ring is preferably 2,2-dimethyl substituted.

Yet in a further most preferred embodiment, $R^4$ is methyl.

The present invention describes five cannabinoid-derived quinones in particular, which were synthesized by the inventors and are referred to herein as 3S,4R-p-benzoquinone-3-hydroxy-2-p-mentha-(1,8)-dien-3-yl-5-pentyl (also designated HU-331), 6aR,10aR-1-H-dibenzo[b,d]pyran-1,4-(6H)-dione-6aβ,7,10,10aα-tetrahydro-6,6,9-trimethyl-3-pentyl (also designated HU-336), 1-H-dibenzo[b,d]pyran-1,4(6H)-dione-6,6,9-trimethyl-3-pentyl (also designated HU-345), 3S,4R-p-benzoquinone-3-hydroxy-2-[p-mentha-1-en-3-yl]-5-pentyl (also designated HU-395), and 3S,4R-p-benzoquinone-3-hydroxy-2-[p-menthan-3-yl]-5-pentyl (also designated HU-396). The first two compounds (HU-331 and HU-336) were previously described by the inventors [Mechoulam et al. (1968) id ibid.], whereas the other three compounds, HU-345, HU-395 and HU-396 are novel cannabinoic quinone derivatives.

It may be appreciated that HU-395 is a derivative of formula (III) above, HU-396 is a derivative of formula (IV) above, and HU-345 is a derivative of formula (V) above.

The structure of these compounds is detailed in FIG. 1, wherein HU-331, HU-336 and HU-345 are also referred to as 2, 4 and 6, respectively.

Thus, in very most preferred embodiments, the pharmaceutical composition of the invention comprises as active agent one of HU-331, HU-336, HU-345, HU-395, HU-396 and any combination thereof.

As described in the Examples, the five quinonoid derivatives of cannabinoids (or cannabinoic quinones), which were synthesized by the inventors, were tested for their anti-proliferative activity on human cancer cell lines. These five compounds had anti-proliferative activity in cell lines which originated from various types of cancer, more specifically from lymphomas, mammary gland (breast), prostate, lung, glioblastoma, and colon.

Thus, the pharmaceutical composition of the invention may be for the treatment of hyperproliferative disorders such as carcinomas, lymphomas, melanomas, glioblastomas and sarcomas. Alternatively, the pharmaceutical composition of the invention may be for the treatment of a non-malignant hyperproliferative disorder, for example psoriasis.

The pharmaceutical composition of the invention may optionally further comprise carriers, additives and diluents.

The preparation of pharmaceutical compositions is well known in the art and has been described in many articles and textbooks, see e.g., Remington's Pharmaceutical Sciences, Gennaro A. R. ed., Mack Publishing Co., Easton, Pa., 1990, and especially pp. 1521-1712 therein.

Compounds with anti-cancer activity are often difficult to solubilize. HU-331 exerted a striking anti-tumor effect in vivo, following either sub-cutaneous (s.c.) or intra-peritoneal (i.p.) administration, when solubilized in ethanol:Emulphor®:PBS (1:1:18), suggesting that this solvent enabled its bioavailability at the cancer site.

Thus, in preferred embodiments, the pharmaceutical compositions of the invention comprise a pharmaceutically acceptable vehicle or carrier, particularly a mixture of ethanol:Emulphor®:phosphate buffered saline (PBS), at 1:1:18 v/v ratio. Emulphor® is a polyoxyethylated vegetable oil, a high-molecular-weight ether sulphate which is an anionic emulsifier. A preferred buffer is PBS, but any physiologically compatible buffer may be used, e.g. Hepes, Tris-buffered saline. Poly(ethylene glycol) and cyclodextrins of various types, like alkylated beta-cyclodextrin, for example, are also suitable carriers.

The pharmaceutical compositions of the invention, comprising as active agent cannabinoid quinones, may also be used in the treatment of conditions such as inflammations, autoimmune diseases (for example multiple sclerosis) and infections, particularly infections caused by infectious agents like bacteria (Gram positive and Gram negative, mycobacteria, etc.), protozoa and fungus.

The compositions of the invention can be administered in a variety of ways. By way of non-limiting example, the composition may be delivered intravenously, or into a body cavity adjacent to the location of a solid tumor, such as the intraperitoneal cavity, or injected directly into or adjacent to a solid tumor. Intravenous administration, for example, is advantageous in the treatment of leukemias, lymphomas, and comparable malignancies of the lymphatic system.

As a preferred route the composition of the present invention may be administered via subcutaneous or intradermal injections in proximity to the tumor, via intratumor or intraperitoneal injection.

The composition of the invention may also be delivered in the form of gelatin capsules, wherein the active agent will be dissolved in poly(ethylene glycols) of the lower molecular weights, suitable for the preparation of said capsules.

The quinones described herein proved to be powerful anti-tumor agents in vivo. As shown in the Examples, nude mice which developed a tumor after the injection of tumor cell lines, had the tumor size significantly decreased after administration of HU-331.

Hence, in another aspect, the present invention relates to a method for the treatment of a hyperproliferative disorder, malignant or non-malignant, comprising administering a therapeutic effective amount of a cannabinoic quinone or of a pharmaceutical composition thereof to a subject in need. Preferred cannabinoic quinones are those represented by one of formulae (I), (II), (III), (IV) and (V) as described above. As detailed below, most preferred cannabinoic quinones are HU-331, HU-336, HU-345, HU-395 and HU-396, and particularly HU-331.

Said therapeutic effective amount, or dosage, is dependent on severity and responsiveness of the disease state to be treated, with the course of treatment lasting from several days to several months, or until a cure is effected or a diminution of the disease state is achieved. The therapeutic effective dosage may be determined by various methods, including generating an empirical dose-response curve, predicting potency and efficacy of a congener by using quantitative structure activity relationships (QSAR) methods or molecular modeling, and other methods used in the pharmaceutical sciences. Optimal dosing schedules may also be calculated from measurements of drug accumulation in the body of the patient. Persons of ordinary skill can easily determine optimum dosages, dosing methodologies and repetition rates. In general, dosage is from 0.01 µg to 100 g per kg of body weight, and may be given once or more daily, weekly, or monthly. Persons of ordinary skill in the art can easily estimate repetition rates for dosing based on the patient's response to the active agent.

The cannabinoic quinone to be used in the method of treatment of the invention is preferably one of the compounds synthesized by the inventors, i.e., HU-331, HU-336, HU-345, HU-395 and HU-396.

Malignant hyperproliferative or proliferative disorders that may be treated by the method of the invention are, for example, carcinoma, lymphoma, melanoma, glioblastoma or sarcoma.

As used herein, "tumor", "cancer" and "malignant hyperproliferative (or proliferative) disorder" all relate equivalently to a hyperplasia of a tissue or organ. If the tissue is part of the lymphatic or immune systems, malignant cells may include non-solid tumors of circulating cells. Malignancies of other tissues or organs may produce solid tumors. In general, the compounds of the present invention as well as the method of the present invention may be used in the treatment of non-solid and solid tumors.

All five compounds inhibited the in vitro growth of human cancer cell lines, with different potency. The cannabinoic quinones of the invention displayed a carcinostatic effect that had not been previously demonstrated.

Figure 5A:
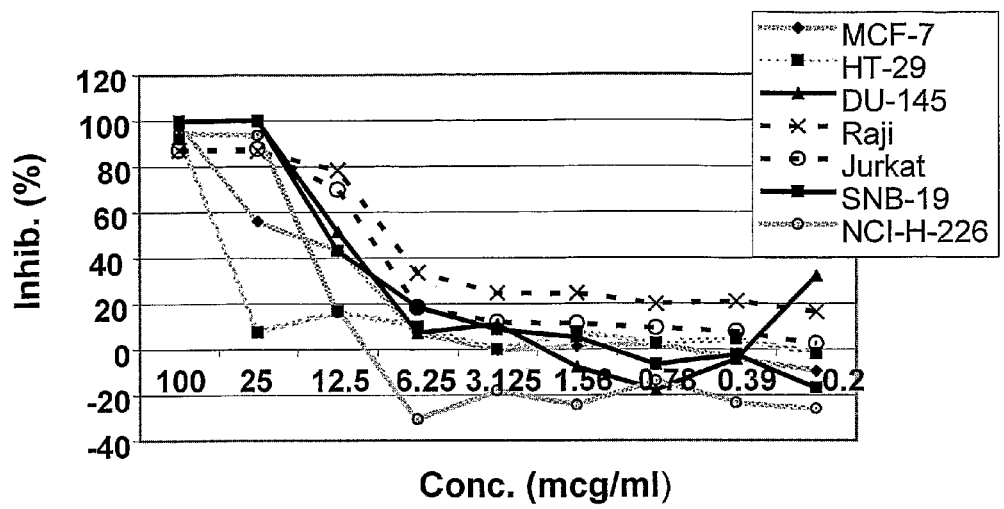
FIG. 5A-5E: The results of MTT test-inhibition of human cancer cell lines by cannabinoic quinones.
Figure 5B:
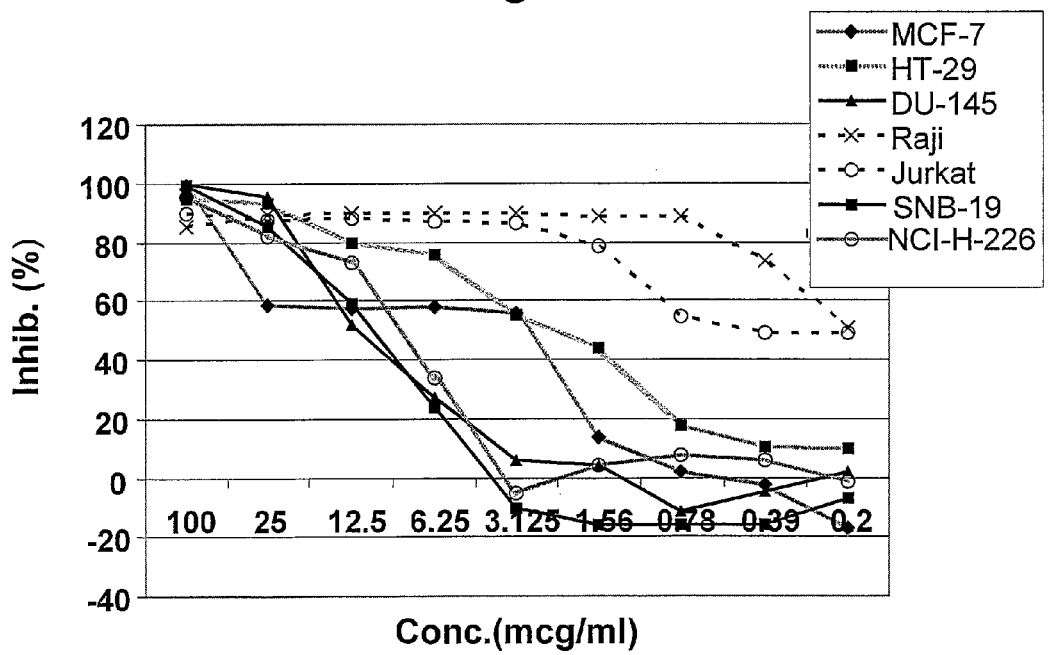

As shown in the Examples, the most potent anti-cancer activity was displayed by HU-331 (2) and HU-395. An inhibition of 50% of the growth of the Raji and Jurkat lymphomas was obtained at a concentration of HU-331 as low as 0.2 µg/ml, while 50% inhibition of the growth of HT-29 colon cancer and of MCF-7 mammary cancer cells required a concentration of 3.125 µg/ml (FIG. 5B). HU-395 displayed almost 60% inhibition of Jurkat cells growth at a concentration of 0.2 µg/ml (see FIG. 5D)

Thus, the present invention provides a cannabinoic quinone, preferably HU-331, or compositions comprising the same, to be used in the treatment of hyperproliferative disorders, particularly colon cancer, lymphoma and breast cancer.

HU-331 displayed a marked anti-cancer activity not only in vitro but also in vivo, in experiments where nude mice received a subcutaneous inoculation of HT-29 colon carcinoma cells (see Example 3). The administration of HU-331 at a concentration that did not have observable adverse effects on the hosts resulted in significant inhibition of the growth of the tumor cells when injected either intraperitoneally (i.p.) or subcutaneously (s.c.) into the region of the tumor graft.

Thus, a major advantage of the cannabinoic quinones described herein (HU-331, HU-336, HU-345, HU-395 and HU-396) is that at concentrations in which they display a medicinal activity, in particular an anti-proliferative activity, these compounds do not have any measurable side-effects, such as weight loss, or any toxic cardiac effect. Therefore, HU-331, HU-336, HU-345, HU-395 and HU-396 may be used as anti-tumor or anti-cancer agents.

Hence, the present invention provides an alternative for cancer treatment, through the use of the cannabinoic quinones described in the invention, with clear benefits for the patient in need of said treatment.

In a further aspect, the present invention provides a method for the treatment of conditions selected from the group consisting of inflammations, autoimmune diseases (in particular multiple sclerosis), and infections, particularly infectins caused by infectious agents such as bacteria (including gram positive and gram negative bacteria, mycobacteria, etc.), protozoa and fungus, wherein said method comprises administering a therapeutic effective amount of a cannabinoic quinone or of a pharmaceutical composition thereof to a subject in need. Preferred cannabinoic quinones are those represented by one of formulae (I), (II), (III), (IV) and (V) as described above. Most preferred cannabinoic quinones are HU-331, HU-336, HU-345, HU-395 and HU-396.

Most importantly, the cannabinoids herein described do not demonstrate any measurable psychotropic effects. The cannabinoic quinones were not able to bind to the cannabinoid receptors CB1 and CB2, up to 15 µM. For comparison, the binding constant of tetrahydrocannabiol is 50 nM.

In one embodiment, HU-331 is the cannabinoic quinone to be used in the method of treatment of the invention, particularly when the proliferative disorder to be treated is colon cancer. Alternatively, this compound is also preferred for the treatment of lymphoma and/or breast cancer.

As shown in Example 3, HU-336, HU-345 and HU-396 required higher concentrations to display their anti-proliferative activity.

HU-336 (4), at a concentration of 12.5 µg/ml or higher, inhibited 50% or more the growth of all the cells tested. The growth of SNB-19 cells was inhibited by HU-336 only at a concentration of 100 µg/ml.

HU-345 (6) was a more potent anti-cancer reagent than HU-336. Raji lymphoma cells growth was inhibited by over 50% at a concentration of 6.25 µg/ml, while that Jurkat lymphoma cells and DU-145 prostate cancer cells were inhibited by a concentration of 12.5 µg/ml. At concentrations of 25.0 µg/ml of HU-345, all cell lines tested were inhibited.

Interestingly, the growth of cell lines SNB-19 and DU-145 was more effectively inhibited by HU-336 and HU-345 than by HU-331.

Thus, in another embodiment, HU-336 and/or HU-345 are to be used in the method of the invention, particularly when the hyperproliferative disorder to be treated is prostate cancer or glioblastoma.

In a later aspect, the present invention also presents the use of a cannabinoic quinone for the preparation of a pharmaceutical composition, or a medicament, wherein said cannabinoic quinone is represented by any one of formulae (I), (II), (III), (IV), and (V) above. Preferably, said cannabinoic quinone is one of HU-331, HU-336, HU-345, HU-395 and HU-396. Most preferably, said cannabinoic quinone is HU-331.

Said pharmaceutical composition may be for the treatment of conditions such as inflammatory, infectious or autoimmune disorders, and in particular for the treatment of hyperproliferative disorders.

Lastly, the present invention provides compounds of formulae (III), (IV) and (V). Compounds of formulae (III) and (IV) are:

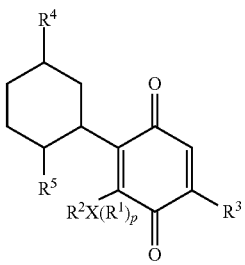

(III)

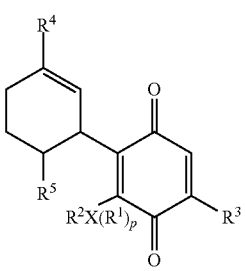

(IV)

wherein
X is an oxygen, nitrogen or sulfur atom;
p is zero when X is oxygen or sulfur, or p is 1 when X is nitrogen;
$R^1$ is H or $C_1$-$C_5$ alkyl;
$R^2$ designates a substituent selected from H and $C_1$-$C_5$ alkyl;
$R^3$ is optionally branched $C_1$-$C_{10}$ alkyl or optionally branched $C_1$-$C_{10}$ alkenyl, wherein said alkyl or alkenyl are optionally substituted with hydroxyl, alkoxy, halo (fluoro, chloro, bromo, iodo), thio, amino or cyano; and
$R^4$ is optionally branched $C_1$-$C_5$ alkyl or optionally branched $C_1$-$C_5$ alkenyl, optionally substituted with hydroxyl, halo (fluoro, chloro, bromo, iodo) thio, amino and cyano; and
$R^5$ is optionally branched $C_1$-$C_5$ alkyl or optionally branched $C_1$-$C_5$ alkenyl.

Compound of formula (V) is:

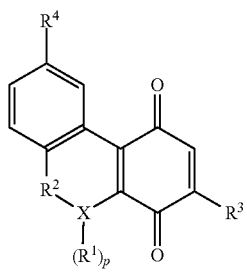

(V)

wherein,
X is an oxygen, nitrogen or sulfur atom;
p is zero when X is oxygen or sulfur, or p is 1 when X is nitrogen;
$R^1$ is H or $C_1$-$C_5$ alkyl;
$R^2$ designates a methylene group optionally substituted with up to two alkyl groups, wherein $R^2$ with the substituents comprises up to 5 carbon atoms;
$R^3$ is optionally branched $C_1$-$C_{10}$ alkyl or optionally branched $C_1$-$C_{10}$ alkenyl, wherein said alkyl or alkenyl are optionally substituted with hydroxyl, alkoxy, halo (fluoro, chloro, bromo, iodo), thio, amino or cyano; and
$R^4$ is optionally branched $C_1$-$C_5$ alkyl or optionally branched $C_1$-$C_5$ alkenyl, optionally substituted with hydroxyl, halo (fluoro, chloro, bromo, iodo) thio, amino and cyano.

Preferred compounds of formulae (III) and (IV) are 3S,4R-p-benzoquinone-3-hydroxy-2-[p-mentha-1-en-3-yl]-5-pentyl and 3S,4R-p-benzoquinone-3-hydroxy-2-[p-menthan-3-yl]-5-pentyl, of formulae:

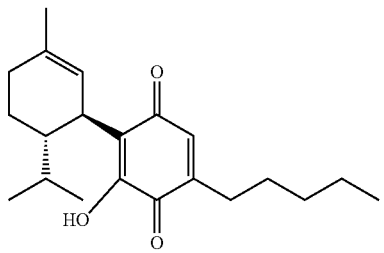 [SMILES: CCCCCC1=CC(=O)C([C@@H]2C=C(C)CC[C@H]2C(C)C)=C(O)C1=O]

also designated HU-395; and

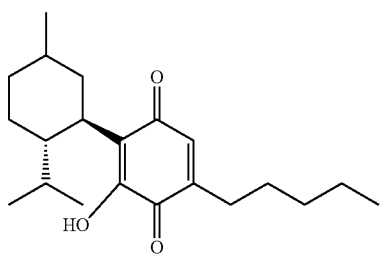 [SMILES: CCCCCC1=CC(=O)C([C@@H]2CC(C)CC[C@H]2C(C)C)=C(O)C1=O]

also designated HU-396, respectively.

The preferred compound of formula (V) is 1-H-dibenzo[b,d]pyran-1,4(6H)-dione-6,6,9-trimethyl-3-pentyl, of formula:

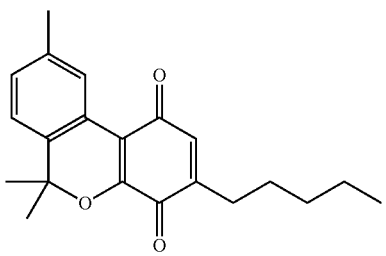 [SMILES: CCCCCC1=CC(=O)C2=C(OC(C)(C)c3ccc(C)cc32)C1=O]

also designated HU-345.

The mechanism of the anti-cancer activity of cannabinoic quinones is still unclear. However, a number of mechanisms have been suggested by which quinones may exert cell damage [Ollinger., K. and Kagedal., K. (2002) *Subcell Biochem.* 36, 151-70]. These include redox cycling, DNA damage and inhibition of topoisomerase, protein damage and lipid peroxidation. Similar mechanisms were shown to mediate the antitumor effects of adriamycin and daunorubicin, which have been in clinical use for the treatment of solid tumors for over 30 years [Gewirtz, D. A. (1999) *Biochem Pharmacol.* 57, 727-41]. The present study clearly indicates that cannabinoic quinones possess a high potential for development into anticancer drugs that may prove effective not only against lymphoma cells but also against solid tumors, with no undesired effects.

In sum, the present invention relates to the medical use of cannabinoic quinones, especially HU-331, HU-336, HU-345, HU-395 and HU-396, as active agents in pharmaceutical compositions. Said compounds are intended for the treatment of inflammatory, infectious, auto-immune and particularly hyperproliferative disorders. Thus, the compounds of the invention may be used as anti-tumor agents, or for the treatment of cancer. In addition, the present invention describes three novel cannabinoic quinones, HU-345, HU-395 and HU-396, which are also claimed herein.

The present invention is defined by the claims, the contents of which are to be read as included within the disclosure of the specification.

Disclosed and described, it is to be understood that this invention is not limited to the particular examples, process steps, and materials disclosed herein as such process steps and materials may vary somewhat. It is also to be understood that the terminology used herein is used for the purpose of describing particular embodiments only and not intended to be limiting since the scope of the present invention will be limited only by the appended claims and equivalents thereof.

It must be noted that, as used in this specification and the appended claims, the singular forms "a", "an" and "the" include plural referents unless the content clearly dictates otherwise.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The following Examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

EXAMPLES

Experimental Procedures

1. Chemical Synthesis

All chemical reagents were purchased from Sigma-Aldrich. Organic solvents were purchased from Bio-Lab. The cannabinoids were extracted from *Cannabis sativa* plant as previously described [Gaoni, Y. and Mechoulam, R. (1971) *J. Amer. Chem. Soc.* 93, 217-224].

1.1. Oxidation of cannabidiol (CBD) to 3S,4R-p-Benzoquinone-3-hydroxy-2-p-mentha-(1,8)-dien-3-yl-5-pentyl (Herein Referred to as HU-331) with KOHaq CBD (1 g, 3.18 mmole) was dissolved in 90 ml petroleum ether (40-60° bp) and 5% KOHaq in ethanol (10 ml, 8.77 mmole) was added. The reaction mixture was stirred at 0° C. in an open beaker for 3 hours, and after, 25 ml of 5% HCl was poured into it. The organic layer was washed with sodium bicarbonate and water and dried ($MgSO_4$). Removal of the solvent under reduced pressure yielded a glassy oil (1.08 g). HU-331 was eluted on column chromatography with petroleum ether-ether (95:5). After crystallization from heptane, 211 mg (0.64 mmole, 20.2% yield) of large brown crystals were obtained.

m.p. (melting point): 50-51° C.

MS (mass spectrometry): 328, 313, 311, 237, 204.

$^1$H NMR: 2H (5.08 ppm), 3H (3.60 ppm), 4H (2.75 ppm), 5H (1.95 ppm, 2.07 ppm), 6H (1.67 ppm, 1.71 ppm), 7H (1.67 ppm), 9H (4.501 ppm, 4.442 ppm), 10H (1.546 ppm), 4'H (6.415 ppm), 1"H (2.306 ppm), 2"H (1.425 ppm), 3"H (1.263 ppm), 4"H (1.263 ppm), 5"H (0/849 ppm), OH (in d6-DMSO, 10.396 ppm).

$[\alpha]_D$: −110° (ethanol, 0.1% w/v)

1.2. Oxidation of $\Delta^8$-THC to 6aR,10aR-1-H-Dibenzo[b,d]pyran-1,4-(6H)-dione-6aβ,7,10,10aα-tetrahydro-6,6,9-trimethyl-3-pentyl (Herein Referred to as HU-336) with CuCl To a solution of $\Delta^8$-THC (104 mg, 0.33 mmole) in 0.9 ml acetonitril (ACN) CuCl (5.5 mg, 0.056 mmole) was added. A thin current of air was bubbled through the mixture for 1.5 h after which 50 ml ether was added. The reaction mixture was washed with $H_2O$, dried ($MgSO_4$) and concentrated. The yellowish oil obtained was purified by column chromatography using pet.ether-ether (95:5) solution. HU-336 (33 mg, 0.1 mmole, 30.5% yield) was obtained as a yellow oil and crystallized from heptane to obtain very thin yellow needles.

m.p.: 53-54° C.

MS: 328, 313, 285, 272, 229, 204.

$^1$H NMR: 2H (6.3 ppm), 6aH (1.61 ppm), 7H (1.76 ppm, 2.06 ppm), 8H (5.33 ppm), 10H (2.92 ppm, 1.67 ppm), 10aH (2.44 ppm), 11H (1.62 ppm), 12H (1.42 ppm), 13H (1.08 ppm), 1'H (2.31 ppm), 2'H (1.438 ppm), 3'H (1.27 ppm), 4'H (1.27 ppm), 5'H (0.84 ppm).

$[\alpha]_D$: −231° (ethanol, 0.22% w/v)

1.3. Oxidation of $\Delta^8$-THC to HU-336 with bis-[(trifluoroacetoxy)iodo]benzene (BTIB)

To a solution of $\Delta^8$-THC (50.1 mg, 0.16 mmole) in ACN/$H_2O$ (6:1, 0.7 ml) a solution of BTIB (215 mg, 0.5 mmole) in 0.7 ml ACN/$H_2O$ (6:1) was added drop wise. The reaction mixture was stirred at room temperature for 15 min, neutralized with aq.$NaHCO_3$ saturated solution and extracted with diethyl ether. The organic layer was washed with $H_2O$, dried ($MgSO_4$) and concentrated. After the purification by column chromatography and crystallization HU-336 (16.75 mg, 0.051 mmole, 31.9% yield) was obtained.

1.4. Oxidation of CBN to 1-H-Dibenzo[b,d]pyran-1,4 (6H)-dione-6,6,9-trimethyl-3-pentyl (Herein Referred to as HU-345) with CuCl To a solution of CBN (95 mg, 0.31 mmole) in 0.9 ml ACN CuCl (10.8 mg, 0.11 mmole) was added. A thin current of air was bubbled through the mixture for 6 h after which 50 ml ether was added. The reaction mixture was washed with $H_2O$, dried ($MgSO_4$) and concentrated. The red oil obtained was purified by column chromatography using a petroleum ether-ether (93:7) solution. HU-345 (15 mg, 0.046 mmole, 15% yield) was obtained as red oil and crystallized from heptane to obtain large red crystals.

m.p.: 81-82° C.

MS: 324, 309, 281, 225, 128.

$^1$H NMR: 2H (6.48 ppm), 7H (7.08 ppm), 8H (7.17 ppm), 10H (8.19 ppm), 11H (2.18 ppm), 12H (1.7 ppm), 13H (1.7 ppm), 1'H (2.44 ppm), 2'H (1.54 ppm), 3'H (1.35 ppm), 4'H (1.35 ppm), 5'H (0.91 ppm).

1.5. Oxidation of CBN to HU-345 with BTIB

To a solution of CBN (50 mg, 0.16 mmole) in ACN/$H_2O$ (6:1, 0.7 ml) a solution of BTIB (215 mg, 0.5 mmole) in 0.7 ml ACN/$H_2O$ (6:1) was added drop wise. The reaction mixture was stirred at room temperature for 15 min, neutralized with aq. $NaHCO_3$ saturated solution and extracted with diethyl ether. The organic layer was washed with $H_2O$, dried ($MgSO_4$) and concentrated. After the purification by column chromatography and crystallization, HU-345 (29.1 mg, 0.09 mmole, 56.1% yield) was obtained.

m.p.: 81-82° C.

MS: 324, 309, 281, 225, 128.

$^1$H NMR: 2H (6.48 ppm), 7H (7.08 ppm), 8H (7.17 ppm), 10H (8.19 ppm), 11H (2.18 ppm), 12H (1.7 ppm), 13H (1.7 ppm), 1'H (2.44 ppm), 2'H (1.54 ppm), 3'H (1.35 ppm), 4'H (1.35 ppm), 5'H (0.91 ppm).

1.6 Reductive Acetylation of HU-336 to the Diacetate

HU-336 (16.9 mg, 0.052 mmole) was dissolved in a solution of $Ac_2O$ (acetic anhydride) (0.7 ml) and AcOH (acetic acid) (0.7 ml). Zn (0.054 g, 0.83 mmole) was added and the mixture was boiled under reflux for 30 minutes. The residue was filtered off, pyridine (2.2 ml) was added to the filtrate and the solution was left at room temperature overnight under $N_2$ atmosphere. After that, the solution was poured into ice-cold 5% HCl, the organic layer was washed with $NaHCO_3$ and water, dried ($MgSO_4$) and concentrated. The obtained oil (20 mg) was purified by column chromatography. The diacetate (10 mg, 0.024 mmole, 46.5% yield) was eluted with petroleum-ether-ether (90:10).

MS: 414, 372, 330, 287, 262, 247, 209.

$^1$H NMR: 2H (6.44 ppm), 6aH (1.75 ppm), 7H (1.77 ppm, 2.1 ppm), 8H (5.33 ppm), 10H (1.36 ppm, 2.7 ppm), 10aH (2.65 ppm), 11H (1.68 ppm), 12H (1.36 ppm), 13H (1.08 ppm), acetate H (2.27 ppm, 2.29 ppm).

1.7. Oxidation of 8,9 dihydrocannabidiol to 3S,4R-p-Benzoquinone-3-hydroxy-2-[p-mentha-1-en-3-yl]-5-pentyl (Herein Referred to as HU-395) with BTIB To a solution of 8,9-dihydrocannabidiol (prepared from plant cannabidiol as previously described [Gaoni, Y. and Mechoulam, R. (1969) *Israel Journal of Chemistry*, 6; 679-690])(50.1 mg, 0.16 mmole) in acetonitrile/$H_2O$ (6:1, 0.7 ml) a solution of BTIB (215 mg, 0.5 mmole) in 0.7 ml acetonitrile/$H_2O$ (6:1) was added drop wise. The reaction mixture was stirred at room temperature for 15 minutes, neutralized with aq. $NaHCO_3$ saturated solution and extracted with diethyl ether. The organic layer was washed with $H_2O$, dried ($MgSO_4$) and concentrated. After the purification by column chromatography 8,9-dihydrocannabidiol-hydroxyquinone (HU-395) (12.3 mg) was obtained.

MS: 330, 315, 287, 273, 247, 231

$^1$H NMR: 2H (5.21 ppm), 3H (3.82 ppm), 4H (2.21 ppm), 5H (1.95 ppm, 2.10 ppm), 6H (1.69 ppm, 1.82 ppm), 7H (1.69 ppm), 4'H (6.25 ppm), 1"H (2.31 ppm), 2"H (1.43 ppm), 3"H (1.27 ppm), 4"H (1.27 ppm), 5"H (0.92 ppm).

1.8. Oxidation of 1,2,8,9 tetarhydrocannabidiol to 3S,4R-p-benzoquinone-3-hydroxy-2-[p-menthan-3-yl]-5-pentyl (Herein Referred to as HU-396) with bis-[(trifluoroacetoxy)iodo]benzene (BTIB)

To a solution of 1,2,8,9-tetrahydrocannabidiol (prepared from plant cannabidiol) (50.0 mg, 0.15 mmole) in acetonitrile/$H_2O$ (6:1, 0.7 ml) a solution of BTIB (215 mg, 0.5 mmole) in 0.7 ml acetonitrile/$H_2O$ (6:1) was added drop wise. The reaction mixture was stirred at room temperature for 15 min, neutralized with aq. $NaHCO_3$ saturated solution and extracted with diethyl ether. The organic layer was washed with $H_2O$, dried ($MgSO_4$) and concentrated. After the purification by column chromatography 1,2,8,9-tetrahydrocannabidiol-hydroxyquinone (HU-396) (12.3 mg) was obtained.

MS: 332, 317, 289, 276, 262, 233, 193

$^1$H NMR: 3H (3.82 ppm), 4H (2.21 ppm), 5H (1.95 ppm, 2.10 ppm), 6H (1.69 ppm, 1.82 ppm), 7H (1.69 ppm), 4'H (6.25 ppm), (2.31 ppm), 2"H (1.43 ppm), 3"H (1.27 ppm), 4"H (1.27 ppm), 5"H (0.92 ppm)

2. Biological Evaluation

Raji and Jurkat cells were suspended in RPMI 1640 medium, supplemented with 20% heat-inactivated fetal calf serum (H-I FCS), 2 mM L-glutamine, 100 U/mL penicillin, and 0.01 mg/mL streptomycin at 37° C. in a 5% $CO_2$ humidified atmosphere. Other cell lines were suspended in RPMI 1640 medium, supplemented with 10% H-I FCS, 2 mM L-glutamine, 100 U/mL penicillin, and 0.01 mg/mL streptomycin at 37° C. in a 5% $CO_2$ humidified atmosphere.

2.1 Cell Proliferation Test

Aliquots (200 µL) of suspensions of cancer cells were dispensed into wells of 96-well tissue culture plates at densities of $0.02 \times 10^6$ cells/well. Various concentrations of cannabinoic quinones were introduced into the wells, and their efficacy was tested three days after initiation of the cultures, using the 3-(4,5-dimethylthiazol-2-yl)-2,5-diphenyltetrazolium bromide (MTT) assay. The principle of this assay is that cells which survive following exposure to various compounds can reduce MTT to a dark-colored formazan, while dead cells are incapable of doing so. The assay was performed as described previously [Carmichael, J., et al. (1987) *Cancer Res.* 47, 936-42; Rubinstein, L. V. et al. (1990) *J Natl Cancer Inst.* 82, 1113-8; Rubnov, S. et al. (2001) *J Nat Prod.* 64, 993-6]. In each MTT assay every concentration of the cytotoxic substance was tested in five replicates in microplate wells. Assays with every cell line were carried out in two to three repeated experiments. The inhibitory effect of various compounds was calculated as percentage inhibition in comparison with the values obtained in untreated wells to which vehicle (ethanol 0.5%) was added.

2.2. In Vivo Experiments

Tumors were grafted into nude mice by s.c. flank inoculation of $0.2 \times 10^6$ HT-29 cells in RPMI 1640 medium without FCS. The animals were assigned randomly to various groups and injected via intraperitoneal (i.p.), intratumor or subcutaneous (s.c.) on day 2 or 14 after cells injection with vehicle (1:1:18 v/v ethanol:Emulphor®:PBS) or 5 mg/kg of HU-331. Tumors were measured with external caliper, and their area was calculated by multiplying the length by the width of the tumor.

3. NMR Spectroscopy

NMR data were collected on Varian Unity Inova 500 and 600 MHz spectrometers using the standard pulse sequences and processed with the VNMR software Example 1

Chemistry

The inventors reported that oxidation of cannabidiol (CBD) (1) by air in an alcohol solution in the presence of 5% potassium hydroxide over 24 hours led to the formation of the hydroxy-quinone 2 with about 5-10% yield [Mechoulam, R. et al. (1968) id ibid]. Now, the inventors have found that a slight change in the reaction conditions—lowering the temperature to 0° C.—raised the yield to ~20% and brought the reaction time down to 3 hours (i.e., there was no more starting material after 3 hours) (FIG. 1). The hydroxy-quinone crystallized from heptane. The inventors had previously reported that the quinone 2 is cyclized to the para-quinone 4 under acid conditions [Mechoulam, R. et al. (1968) id ibid]. A different report, however, had suggested that 4 is an ortho-quinone [Hodjat-Kashani et al. (1986) *Heterocycles* 24, 1973-1976], based on a structural assignment using Nuclear Overhauser Effect (NOE) NMR data (see below). If indeed 3 would be an ortho quinone, then 2 would also be an ortho quinone. Nonetheless, the inventors confirmed by x-ray crystallography the structure of 2 as originally proposed (data not shown). Quinone 2 was code named HU-331 (HU=Hebrew University).

Oxidation of $\Delta^8$-tetrahydrocannabinol (THC) (3) with m-chloro perbenzoic acid as originally reported [Mechoulam, R. et al. (1968) id ibid] gave the desired quinone at a low yield. In order to improve the yield the inventors oxidized 3 with the oxidizing agent BTIB, which was not available when the original reaction was performed.

BTIB was first used for oxidation of phenols to quinones [Tamura, Y. et al. (1989) *Synthesis* 126-127] and then became a widely used reagent for the oxidation of phenols to quinones [Akai, S., Kita, Y. (1998) *Org Prep Procedures Inl* 30, 603-629; Barret, R., Daudon, M. (1990) *Tetrahedron Letters* 31, 4871-4872; Kato, N. et al. (1997) *Synthesis* 625-627; Barret, R., Daudon, M. (1990) *Synth commun.* 20, 2907-2912]. BTIB oxidation of $\Delta^8$-THC (3) led to the desired quinone 4 in 30-35% yield (FIG. 1). This compound was code named HU-336.

An interesting feature of the oxidation of 3 is that by using copper chloride in acetonitrile, which commonly leads to the formation of o-quinones [Capdevielle, P. and Maumy, M. (1982) *Tetrahedron Letters* 23, 1577-1580], the same para-quinone 4 is obtained as in the presence of BTIB and at approximately the same yield.

As mentioned above, the inventors originally proposed a para-quinone structure for 4 [Mechoulam, R. et al. (1968) id ibid.], while Hodjat-Kashani et al. proposed an ortho-quinone structure [Hodjat-Kashani, H. et al. (1986) id ibid]. In order to establish the correct structure, a detailed NMR analysis was performed (see below), and confirmed that compound 4 is indeed a para-quinone, as originally suggested.

The quinone of cannabinol (CBN) (6), like the quinone of $\Delta8$-THC (4), was synthesized by oxidation with BTIB, with a yield of ~60%. The structure was determined by x-ray crystallography (data not shown). The compound was code named HU-345.

Example 2

NMR Analysis of HU-336 (4)

1. Assignment of the Proton Spectrum

Figure 2A:
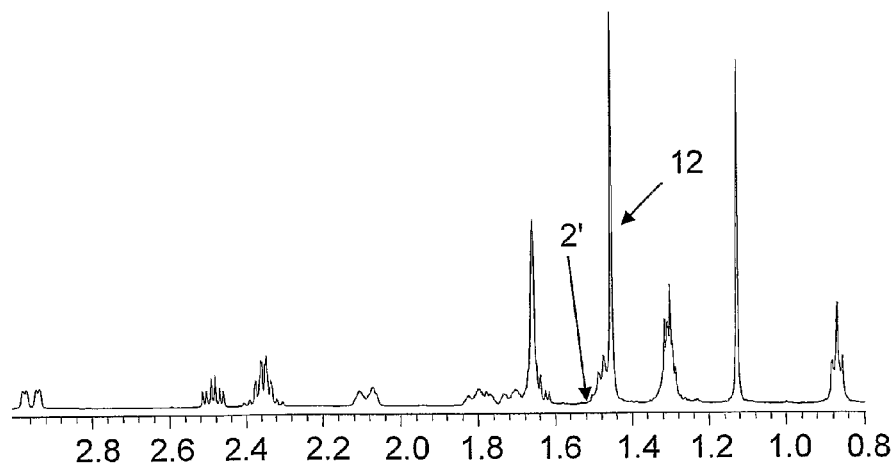
FIG. 2A-2B.
Figure 2B:
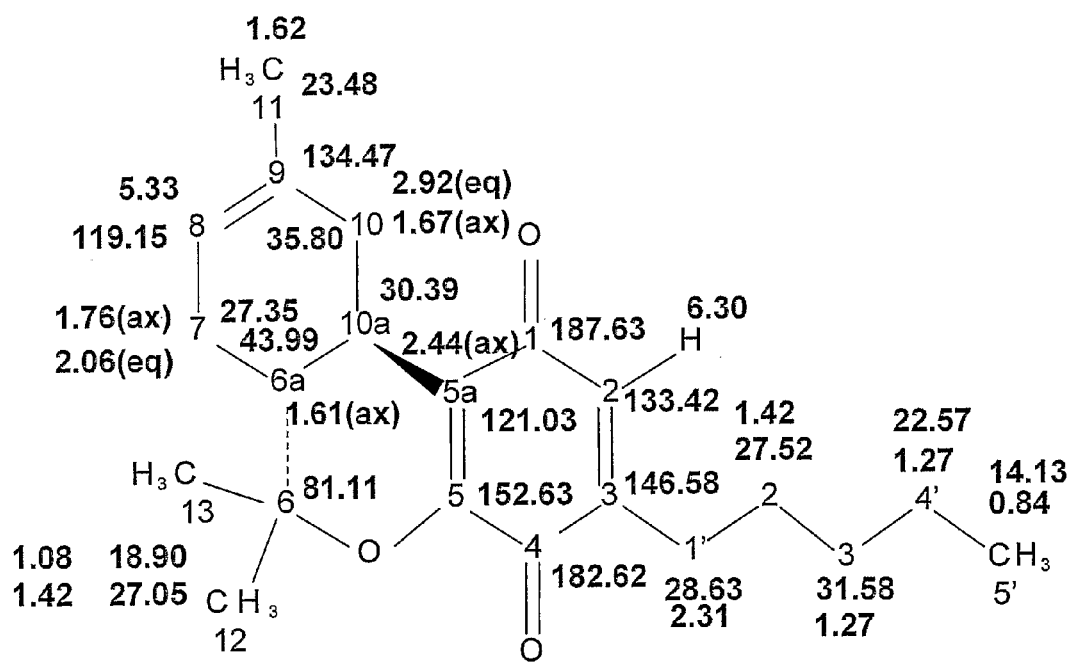

The structure of HU-336 (4) along with the atom labeling scheme and the proton and carbon chemical shifts are depicted in FIG. 2. The 5' methyl group was assigned on the basis of its integration (3H), chemical shift (0.84 ppm) and multiplicity (triplet). Methylene groups 1'-4' were assigned from analysis of the COSY and GHSQC_TOCSY spectra. H2 was assigned on the basis of strong NOESY cross peaks to 1' and 2', its chemical shift (6.30 ppm) and its multiplicity, a triplet with a 1.36 Hz coupling constant indicating long range coupling to 1'. The assignment of the H2 resonance does not allow determining whether the two carbonyls are ortho or para to each other (vide infra). The broad peak at 5.33 ppm was assigned to H8 on the basis of its chemical shift. The remaining resonances of the spin system (H7, H6a, H10a and H10) were assigned on the basis of standard analysis of COSY, NOESY, TOCSY and GHSQC [for review see Reynolds, W. F. and Enriquez, R. G. (2002) *J. Nat. Prod.* 65, 221-244]. Methyl group 11 was assigned on the basis of a COSY cross peak to H8 and NOESY cross peaks to H8 and H10. No attempt was made to distinguish between the methyl groups 12 and 13 (resonating at 1.08 and 1.42 ppm).

2. Assignment of the Carbon Spectrum

Protonated carbons were assigned by analysis of the HSQC spectrum in a straightforward manner. The assignments of the two non-equivalent protons of H10 (2.92 and 1.67 ppm) were confirmed by their cross peaks to the same carbon resonance (35.80 ppm). Similarly, the two non-equivalent protons of H7 (2.06 and 1.76 ppm) were confirmed by cross peaks to the same carbon resonance (27.35 ppm). $C_3$ was assigned on the basis of cross peaks to H7, H1' and H2' in the HMBC spectrum. $C_5$ was assigned on the basis of its low field chemical shift (152.63 ppm) and it HMBC cross peaks to H10a (2.44 ppm) and to the methyl group at 1.42 ppm. $C_9$, $C_6$ and $C_{5a}$ were assigned on the basis of the analysis of the HMBC spectrum. The two carbonyls have resonances at 182.62 and 187.63 ppm.

3. Determining the Correct Configuration

Figure 4:
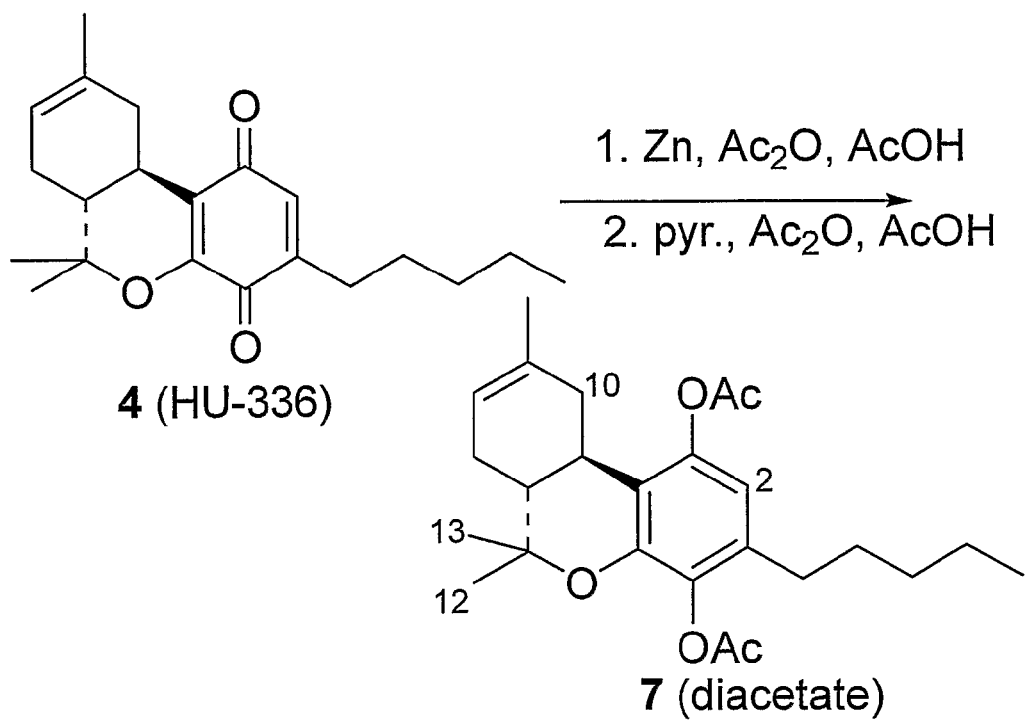
FIG. 4: The reductive acetylation of HU-336.

Due to the above-mentioned conflicting reports in the literature [Mechoulam, R. et al. (1968) id ibid; Hodjat-Kashani, H. et al. (1986) id ibid] a detailed NMR study was performed in order to determine in an unequivocal way the correct configuration of HU-336. Towards that end, a two pronged approach was adopted: a) to carry out a detailed high field NMR study of HU-336 and sort out the correct positioning of two carbonyl groups and b) to chemically reduce the two carbonyl groups of HU-336 and then form the corresponding acetates (see FIG. 4), which would provide two additional methyl groups. The latter would then help to determine the configuration by NOE studies.

Figure 3:
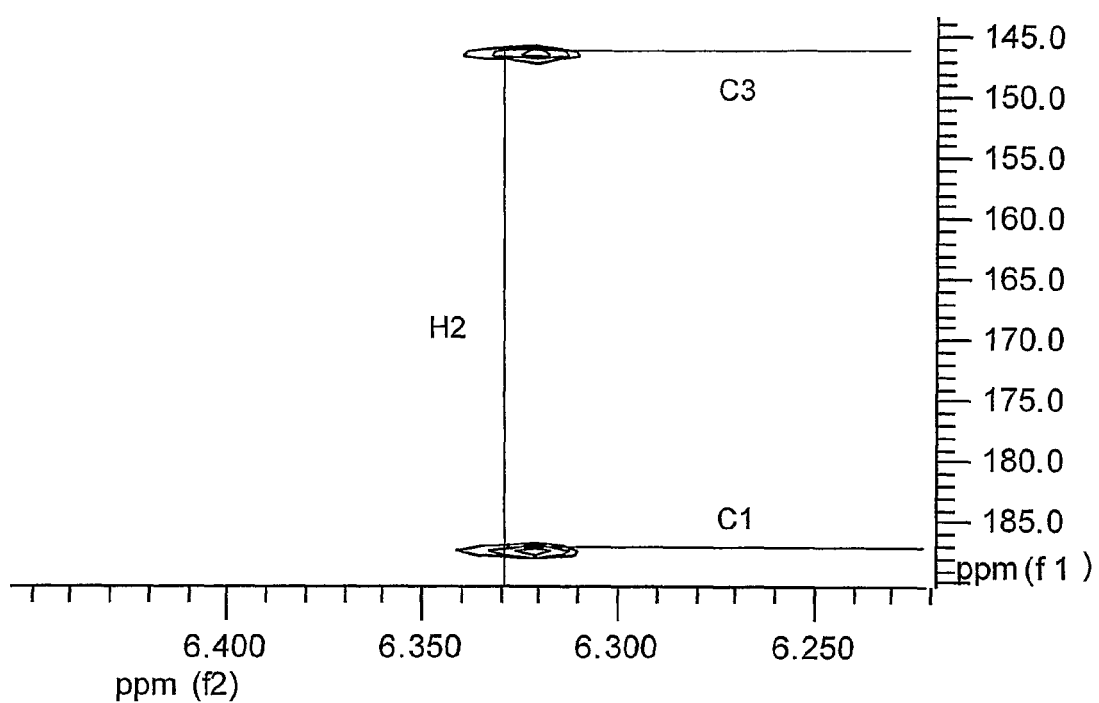
FIG. 3: Adequate of HU-336.

Results of the HMBC experiments demonstrating long range C—H correlations (2-4 bonds) showed that the proton at 6.30 ppm had strong correlations with C1', C5a and the carbonyl at 182.62 and weaker correlations with $C_3$ and $C_5$. Since the intensity, and even the observation of HMBC cross peaks, is not merely a function of the number of bonds separating the two interacting nuclei but also depends on other structural factors (torsional angles and bond order), the data did not allow the inventors to arrive at an unambiguous determination of the configuration. Thus, a further experiment was performed to determine carbon-carbon connectivity. The 1,1-adequate pulse sequence [Köck, M. et al. (1996) *Tetrahedron Letters* 37, 363-366; Reif, B. et al. (1996) *JMR A* 118, 282-285] detected $C_{13}$ single quantum coherences in the indirect domain. The resulting spectrum is similar to that of an HMBC except that only two-bond 13C-1H correlations are obtained. The cross peaks of the resonance at 6.30 ppm are depicted in FIG. 3 clearly demonstrating that the protonated carbon at 133.42 ppm is adjacent to $C_3$ (146.58 ppm) and to a carbonyl at 187.63 ppm. This result is only consistent with the para-configuration, where the protonated carbon $C_2$ is between a sp2 carbon and a carbonyl carbon. This experiment further confirmed the assignment of the $_{13}C$ resonance at 187.63 ppm as $C_1$. If the configuration were to be indeed ortho-, the protonated carbon ($C_4$) would have correlations to $C_3$ (146.58 ppm) and to $C_5$ (152.63 ppm) and there would be no correlation with a carbonyl carbon. The results of the adequate experiment prove beyond doubt that the positioning of the carbonyl groups is indeed para-. Thus, the adequate spectrum confirmed all of the inventor's previous 1H and $_{13}C$ assignments.

To finally ensure that HU-336 (4) is a para-quinone, reductive acetylation with zinc and acetic anhydride was performed. Further confirmation came from the analysis of the NOESY spectrum of the acetylated analog 7 depicted in FIG. 4. The two acetyl methyl groups resonate at 2.27 and 2.29 ppm. The methyl group at 2.27 ppm had NOESY cross peaks to $C_{10}$ (1.67 ppm) and a strong cross peak to H2 (6.30 ppm), and was therefore assigned as $CH_3(1)$. The methyl group at 2.29 ppm had a NOESY cross peak to the methyl group at 1.08, suggesting that it is the $CH_3(4)$ group. An energy minimization of the structure in the ortho geometry revealed that the shortest distance between the acetyl protons in positions 1 and 2 to the methyl protons in positions 12 and 13 is 4.08 Angstrom. This would show weak cross peaks in the NOESY spectrum, while in the para-position the distance is 2.5-3.2 Angstrom, expecting to result in stronger NOE cross peaks.

The present data, measured on a Varian Inova 600 MHz spectrometer, suggest that the proton resonances for the 12 methyl group and the 2' methylene group overlap. Perhaps the close proximity of the chemical shifts (1.420 and 1.438 ppm respectively), which was not properly resolved on the 300 MHz spectrometer (a 5.4 Hz difference), may have been the reason for mistaking [Hodjat-Kashani, H. et al. (1986) id ibid] the NOE between H7 and H2' for the NOE between H4 and the methyl group 12.

Example 3

Biological Activity of the Cannabinoic Quinones

1. In Vitro Activity

The ability of cannabinoic quinones to inhibit cancer growth in vitro was verified on the following human cancer cell lines: Raji (Burkitt's lymphoma), Jurkat (human T-cell lymphoma), SNB-19 (glioblastoma), MCF-7 (breast cancer), DU-145 (prostate cancer), NCI-H-226 (lung cancer), and HT-29 (colon cancer) (see FIG. 5A-5E).

HU-331 (2) exerted an inhibitory effect on the in vitro growth of all seven human cancer cell lines tested (FIG. 5B). The most striking inhibition by HU-331 was found in tests with the Raji and Jurkat lymphoma cells, where an inhibition of about 50% of the growth of both lymphomas was obtained at a concentration of HU-331 as low as 0.2 μg/ml. A concentration of 1.56 μg/ml inhibited the growth of the lymphomas by over 80%. The most sensitive epithelial cancer cells were HT-29 (colon cancer) and MCF-7 (mammary cancer). At a concentration of 3.125 μg/ml, HU-331 inhibited the growth of these cancer cell lines by about 50%.

Figure 5C:
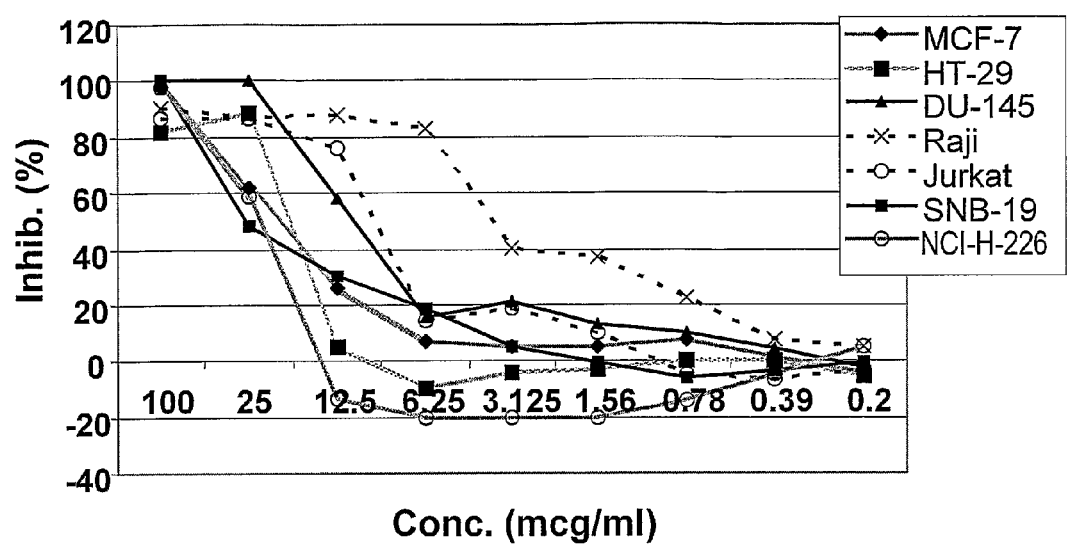

HU-345 (6) inhibited the growth of Raji cells more effectively than that of the other cell lines tested (FIG. 5C). A concentration of 12.5-25.0 μg/ml of HU-345 (6) was required for growth inhibition of Jurkat cells and all other cell lines tested.

HU-336 (4) had the weakest capacity to inhibit the growth of human cancer cell lines in vitro (FIG. 5A), and it exerted a similar inhibitory effect on all cell types, at a concentration over 12.5 μg/ml.

Figure 5D:
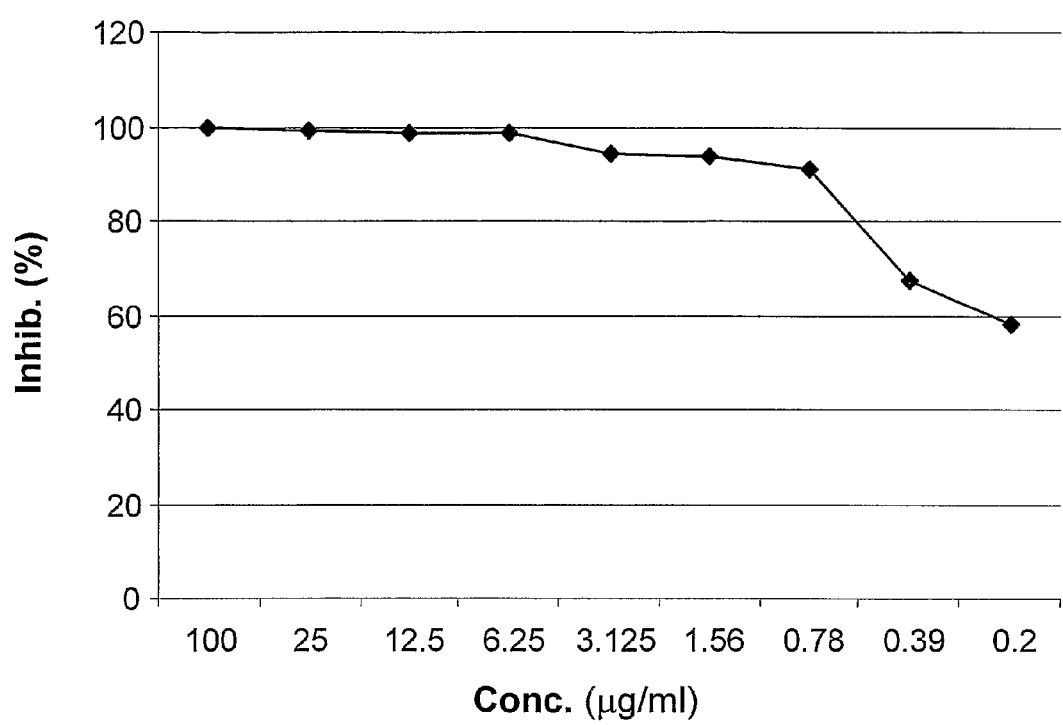
Figure 5E:
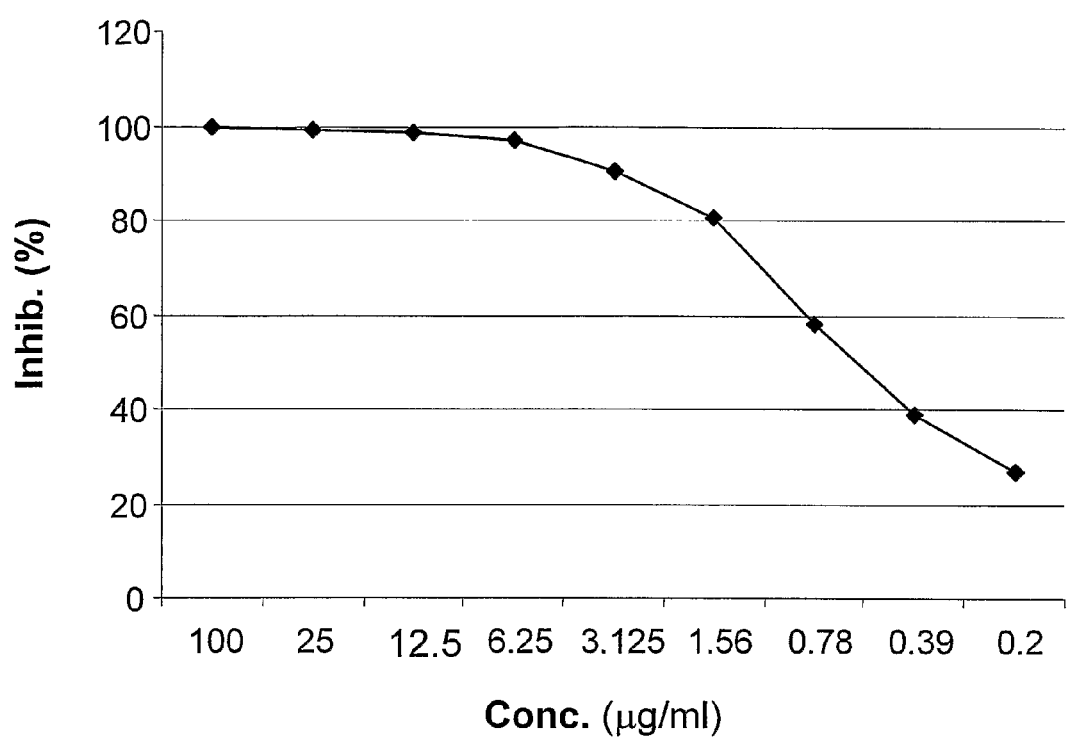
Figure 6A:
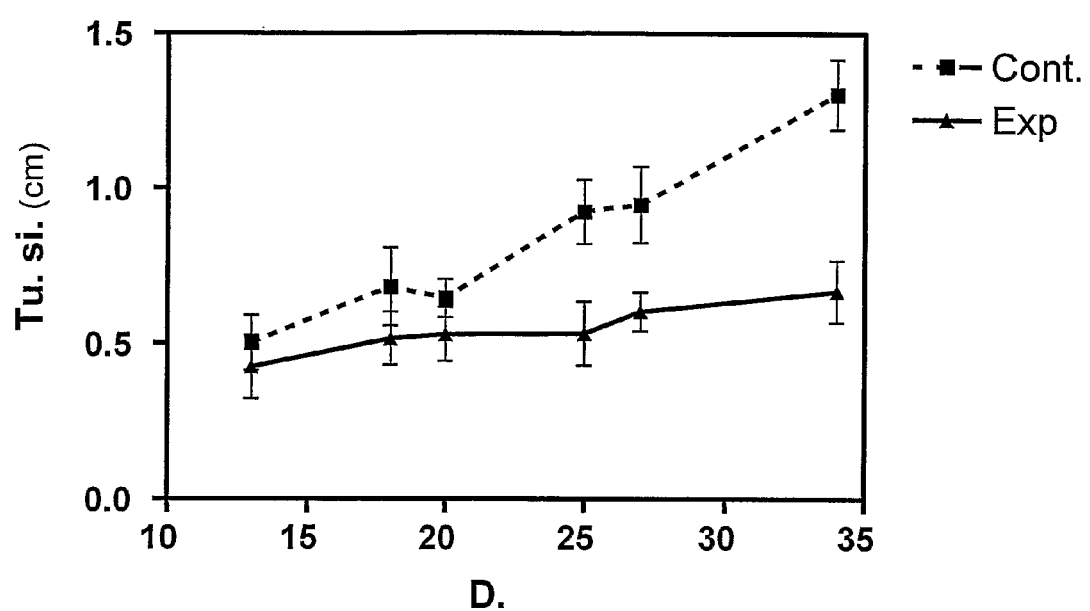
FIG. 6A-6B: The results of in vivo activity of HU-331 on HT-29 cancer growth.
Figure 6B:
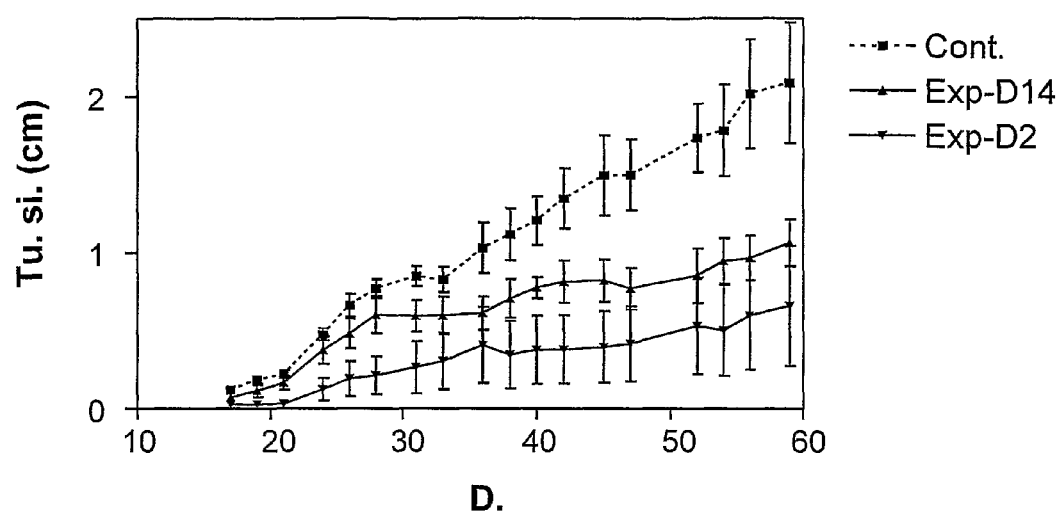
Figure 7A:
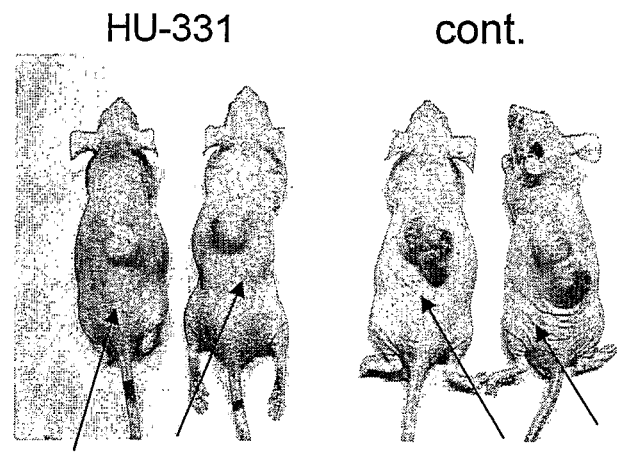
FIG. 7A-7B: Effect of 5 mg/kg of HU-331 (i.p.) in vivo.
Figure 7B:
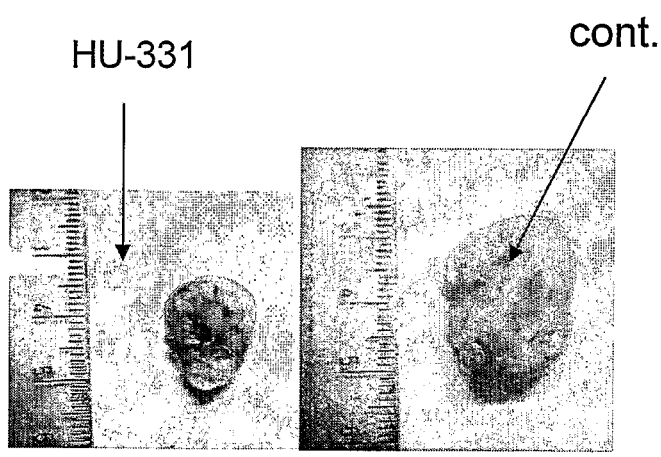

HU-395 was able to inhibit Jurkat cell proliferation at least to the same extent as HU-331, or even a little more effective (FIG. 5D). Noticeably, in the concentration of 0.2 μg/ml HU-395 kills more than 50% of the cancer cells.

HU-396 was able to inhibit Jurkat cell proliferation less effectively than HU-395 and HU-331. At a concentration of 0.78 μg/ml HU-396 kills about 60% of the cancer cells, while at 0.39 μg/ml it kills about 40% of the cells.

Interestingly, the HT-29 and MCF-7 cell lines were the most susceptible to inhibition by HU-331 (2), whereas the SNB-19 and DU-145 cell lines were the most susceptible to inhibition by HU-336 (4) and HU-345 (6).

It is important to note that this is the first report of the medicinal effects of these compounds.

2. In Vivo Activity

A series of experiments were carried out to determine the capacity of HU-331 to inhibit the growth of human tumor cells in vivo. Nude mice received a subcutaneous (s.c.) injection of HT-29 human colon cancer cells. At various time intervals after the administration of the tumor cells the mice received i.p. or s.c. injections of HU-331 (2) at a dose of 5 mg/kg 3 times per week. This concentration paralleled the concentration of 5 μg/ml used in the in vitro experiments, which killed about 50% of HT-29 cancer cells. Treatment of mice with HU-331 at a dose of 5 mg/kg did not cause either weight loss or any observable adverse effects in the treated mice.

Further, ten nude mice received a s.c. injection of HT-29 and were divided in two groups. Starting from day 2 after tumor injection, one group of mice received the i.p. injections of HU-331. The size of tumors was significantly smaller in HU-331 injected mice than in vehicle-treated control mice, starting at 25 days after cancer cells injection (p<0.05, FIG. 6b). At 35 days after cancer cell injection, the tumors in the treated group were half the size of the tumors in controls, a difference that was highly significant (p<0.0029) (FIGS. 6A-6B and 7A-7B).

In another in vivo experiment, two groups of nude mice received an injection of HT-29 cancer cells subcutaneously in their backs. HU-331 (2) was injected subcutaneously at a concentration of 5 μg/ml (FIG. 6). In one group (Group 1), HU-331 was administrated intra-tumorally starting 14 days after the injection of tumor cells. In another group (Group 2), HU-331 was injected subcutaneously in the region where cancer cells had been injected, starting 2 days after the injection of tumor cells. In the mice of Group 2, which received HU-331 starting 2 days after tumor implantation the tumor size was significantly smaller than in control mice at days 17-25 after tumor implantation, and remained significantly smaller until day 59 after tumor transplantation (p<0.05). In the mice that received HU-331 intra-tumorally starting 14 days after tumor implantation (Group 1), the anti-tumor effect of HU-331 took a longer time to be manifested. The tumor size in treated mice was smaller than in controls from day 31 onwards, but this difference was not significant until day 45 after cancer cell injection. Starting at day 45 after cell injection the size of the tumor was significantly smaller than in control mice (p<0.05).

The invention claimed is:

1. A pharmaceutical composition comprising, as an active ingredient, a cannabinoic quinone or an enantiomer thereof, wherein the cannabinoic quinone is a compound of formula (V):

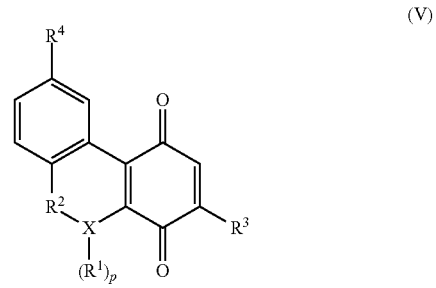

wherein
- X is an oxygen atom;
- p is zero when X is oxygen;
- $R^1$ is H or $C_1$-$C_5$ alkyl;
- $R^2$ designates a methylene group optionally substituted with up to two alkyl groups, wherein $R^2$ with substituents comprises up to 5 carbon atoms;
- $R^3$ is optionally branched $C_1$-$C_{10}$ alkyl or optionally branched $C_1$-$C_{10}$ alkenyl, wherein the alkyl or alkenyl are optionally substituted with hydroxyl, alkoxyl, halo (fluoro, chloro, bromo, iodo), thio, amino, or cyano; and
- $R^4$ is optionally branched $C_1$-$C_5$ alkyl or optionally branched $C_1$-$C_5$ alkenyl, optionally substituted with hydroxyl, halo (fluoro, chloro, bromo, iodo), thio, amino, and cyano.

2. The pharmaceutical composition of claim 1, wherein $R^4$ is methyl.

3. The pharmaceutical composition of claim 1, wherein the cannabinoic quinone is 1-H-dibenzo[b,d]pyran-1,4(6H)-dione-6,6,9-trimethyl-3-pentyl, designated HU-345.

4. The pharmaceutical composition of claim 1, wherein the composition is for therapeutic treatment of a hyperproliferative disorder.

5. The pharmaceutical composition of claim 4, wherein the hyperproliferative disorder is a malignant or a non-malignant disorder.

6. The pharmaceutical composition of claim 4, wherein the hyperproliferative disorder is one of carcinoma, lymphoma, melanoma, glioblastoma, and sarcoma.

7. The pharmaceutical composition of claim 5, wherein the non-malignant hyperproliferative disorder is psoriasis.

8. The pharmaceutical composition of claim 1, wherein the composition is formulated for intra-peritoneal (i.p.), subcutaneous (s.c.), or intratumor administration to a subject in need thereof.

9. The pharmaceutical composition of claim 1, wherein the composition is for therapeutic treatment of a condition selected from inflammation and infections caused by bacteria, protozoa, or fungus.

10. The pharmaceutical composition of claim 1, for therapeutic treatment of an autoimmune disease.

11. The pharmaceutical composition of claim 1, wherein the composition further comprises pharmaceutically acceptable additives, diluents, or carriers.

12. The pharmaceutical composition of claim 1, wherein the active ingredient comprises an optically active isomer or a racemic mixture of the cannabinoic quinone.

13. A compound of formula (V):

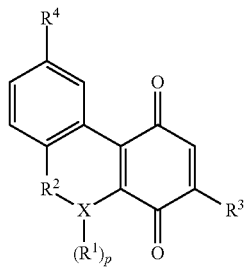

(V)

wherein
- X is an oxygen atom;
- p is zero when X is oxygen;
- $R^1$ is H or $C_1$-$C_5$ alkyl;
- $R^2$ designates a methylene group optionally substituted with up to two alkyl groups, wherein $R^2$ with substituents comprises up to 5 carbon atoms;
- $R^3$ is optionally branched $C_1$-$C_{10}$ alkyl or optionally branched $C_1$-$C_{10}$ alkenyl, wherein the alkyl or alkenyl are optionally substituted with hydroxyl, alkoxyl, halo (fluoro, chloro, bromo, iodo), thio, amino or cyano; and
- $R^4$ is optionally branched $C_1$-$C_5$ alkyl or optionally branched $C_1$-$C_5$ alkenyl, optionally substituted with hydroxyl, halo (fluoro, chloro, bromo, iodo), thio, amino and cyano.

14. The compound of claim 13, wherein the compound has formula:

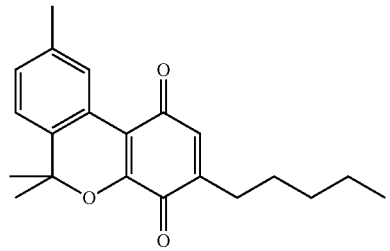 [SMILES: CCCCCC1=CC(=O)C2=C(OC(C)(C)c3ccc(C)cc32)C1=O]

and is designated HU-345.

15. An optically active isomer or racemic mixture of the compound defined in claim 13.

16. An optically active isomer or racemic mixture of the compound defined in claim 14.

17. The pharmaceutical composition of claim 1, wherein the pyrane ring is 2,2-dimethyl substituted.

* * * * *